US009855092B2

(12) United States Patent
Livneh

(10) Patent No.: US 9,855,092 B2
(45) Date of Patent: *Jan. 2, 2018

(54) SCANNING CANNULA

(71) Applicant: Steve Livneh, Amherstburg (CA)

(72) Inventor: Steve Livneh, Amherstburg (CA)

(73) Assignee: RF KINETICS INC., Amherstburg, Ontario (CA)

( * ) Notice: Subject to any disclaimer, the term of this patent is extended or adjusted under 35 U.S.C. 154(b) by 407 days.

This patent is subject to a terminal disclaimer.

(21) Appl. No.: 14/501,818

(22) Filed: Sep. 30, 2014

(65) Prior Publication Data

US 2015/0100053 A1    Apr. 9, 2015

Related U.S. Application Data

(63) Continuation-in-part of application No. 13/127,577, filed as application No. PCT/US2009/064185 on Nov. 12, 2009.

(Continued)

(51) Int. Cl.
    *A61B 18/12*         (2006.01)
    *A61B 18/14*         (2006.01)
    *A61B 18/00*         (2006.01)

(52) U.S. Cl.
    CPC ...... *A61B 18/1482* (2013.01); *A61B 18/1206* (2013.01); *A61B 2018/00083* (2013.01);
(Continued)

(58) Field of Classification Search
    CPC ...... A61B 18/1482; A61B 2018/00178; A61B 2018/00083; A61B 2018/00898;
(Continued)

(56) References Cited

U.S. PATENT DOCUMENTS

| 1,857,857 A | 5/1932 | Medley |
| 3,614,605 A | 10/1971 | Eisele |

(Continued)

FOREIGN PATENT DOCUMENTS

| CN | 1260062 A | 7/2000 |
| CN | 105455896 A | 4/2016 |

(Continued)

OTHER PUBLICATIONS

International Search Report of WO 2010/059501 A1 dated Feb. 1, 2010, 1 page.

(Continued)

*Primary Examiner* — Jaymi Della
*Assistant Examiner* — Eunhwa Kim
(74) *Attorney, Agent, or Firm* — Howard & Howard Attorneys PLLC

(57) ABSTRACT

A scanning cannula for scanning an electrosurgical instrument for electrical insulation defects includes an elongated sleeve having a receiving end, an opposite exit end, and a passageway extending from the receiving end to the exit end. At least one sweeping contact is disposed in the passageway with a limit switch or photocell upstream. A circuit is electrically connected to the at least one sweeping contact. A communication device is connected to the circuit to transmit signals from the circuit to a controller of a surgical instrument. An electrosurgical instrument inserted into the receiving end of the sleeve passes through the at least one sweeping contact, and any electrical defect of the electrosurgical instrument detected by the at least one sweeping contact and assessed by the software is relayed as an error signal to the circuit, which communicates the error signal to the controller. The controller cuts current to the electrosurgical instrument and signals an alarm. The scanning cannula also discloses a cannula with an added capa- (Continued)

bility for testing the insulated shafts of any incoming devices for insulation defects, and not allow electricity to flow to the device from the generator unless the insulation of the shaft has been tested and found to be free of defects (or when the OVERRIDE function is activated). The scanning cannula further may include the use of an attachable scanning chamber to commercially available non-scanning cannulas, thus allowing virtually all users of endoscopic cannulas to add vital safety feature: RF insulation scan as last step before the incoming RF electrosurgical instrument is used on the patient.

20 Claims, 23 Drawing Sheets

Related U.S. Application Data

(60) Provisional application No. 61/116,395, filed on Nov. 20, 2008.

(52) U.S. Cl.
CPC ........... *A61B 2018/00178* (2013.01); *A61B 2018/00708* (2013.01); *A61B 2018/00779* (2013.01); *A61B 2018/00827* (2013.01); *A61B 2018/00898* (2013.01)

(58) Field of Classification Search
CPC .. A61B 2018/00827; A61B 2018/1206; A61B 2018/00708; A61B 2018/00779; A61B 2560/0276; A61B 6/586; A61B 1/00057
USPC ....... 324/508–524, 541, 544, 551, 555, 557, 324/558, 71.1
See application file for complete search history.

(56) References Cited

U.S. PATENT DOCUMENTS

| | | | |
|---|---|---|---|
| 4,477,769 A * | 10/1984 | Lowery | G01R 31/022 324/517 |
| 4,644,610 A | 2/1987 | Fish | |
| 4,857,857 A | 8/1989 | Valenit | |
| 5,312,327 A | 5/1994 | Bales et al. | |
| 5,552,713 A | 9/1996 | Rashidi | |
| 5,676,678 A | 10/1997 | Schad | |
| 5,688,269 A * | 11/1997 | Newton | A61B 18/1233 606/35 |
| 5,908,402 A | 6/1999 | Blythe | |
| 5,936,536 A | 8/1999 | Morris | |
| 6,039,734 A | 3/2000 | Goble | |
| 6,042,573 A | 3/2000 | Lucey | |
| 6,077,290 A | 6/2000 | Marini | |
| 6,376,766 B1 | 4/2002 | Bartholomä et al. | |
| 6,494,880 B1 | 12/2002 | Swanson et al. | |
| 6,977,509 B2 | 12/2005 | Carroll et al. | |
| 7,018,331 B2 | 3/2006 | Chang et al. | |
| 2002/0188173 A1 * | 12/2002 | Kobayashi | A61B 1/00059 600/118 |
| 2007/0179489 A1 | 8/2007 | Dodde et al. | |
| 2011/0221463 A1 | 9/2011 | Livneh | |
| 2014/0100478 A1 | 4/2014 | Speeg et al. | |

FOREIGN PATENT DOCUMENTS

| | | |
|---|---|---|
| EP | 3 002 595 A1 | 4/2016 |
| WO | 98/45822 A2 | 10/1998 |

OTHER PUBLICATIONS

Office Action dated Mar. 5, 2013 of Chinese Application No. 200980146205.8 and English Translation which corresponds to parent U.S. Appl. No. 13/127,577.

English language abstract for CN1260062 extracted from espacenet.com on Apr. 16, 2013, 1 page.

Extended Search Report dated Jul. 7, 2016.

* cited by examiner

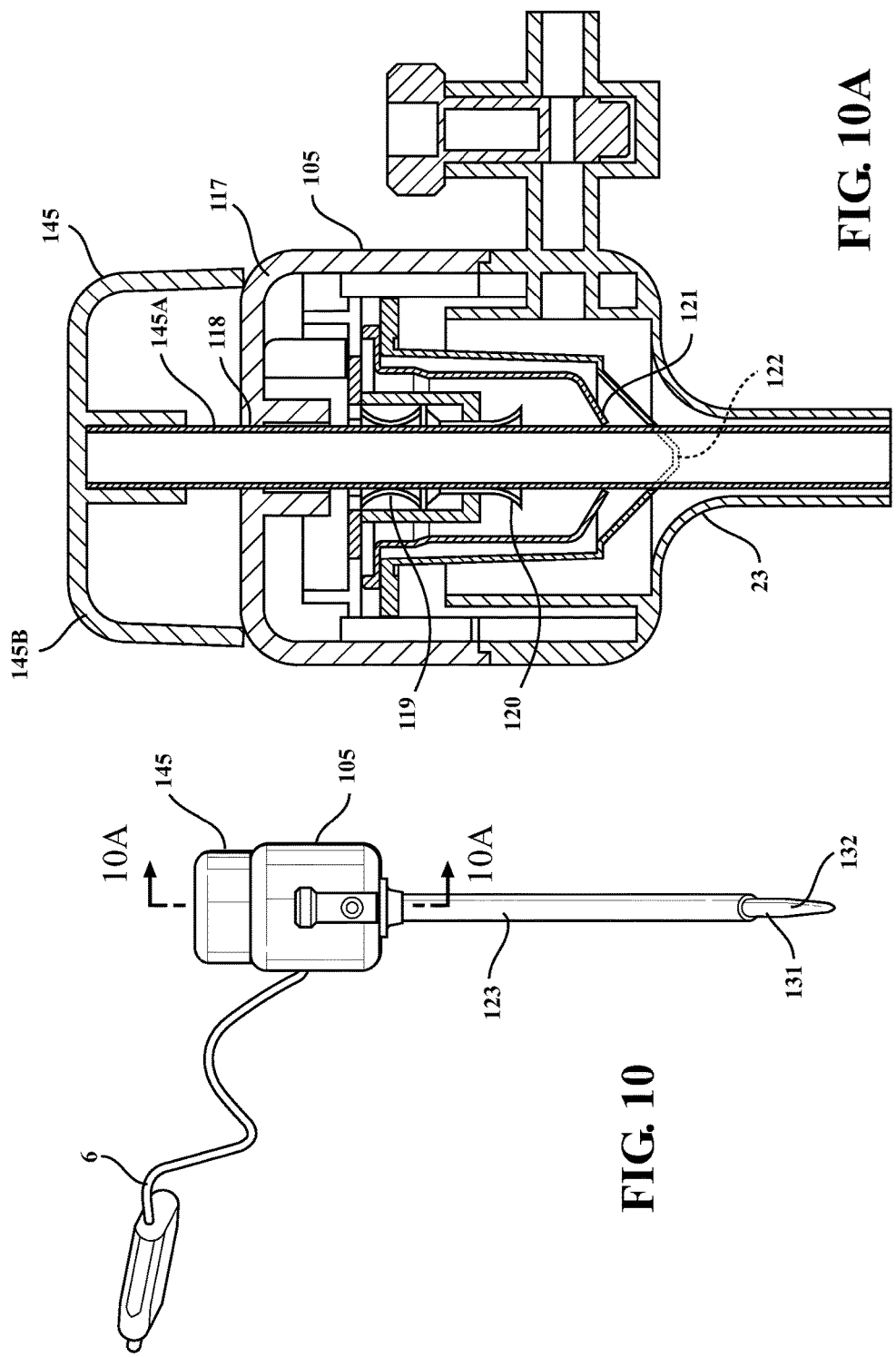

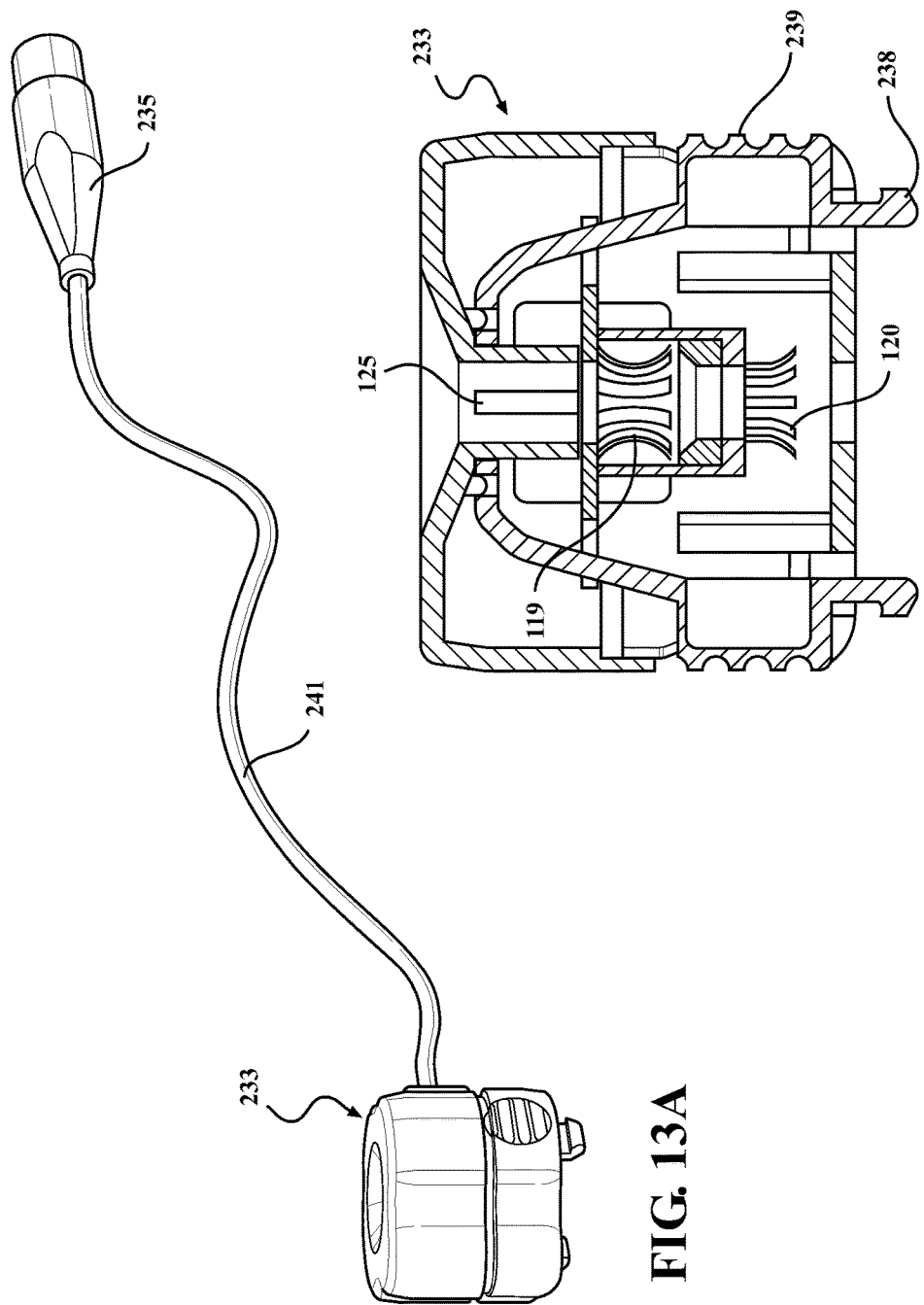

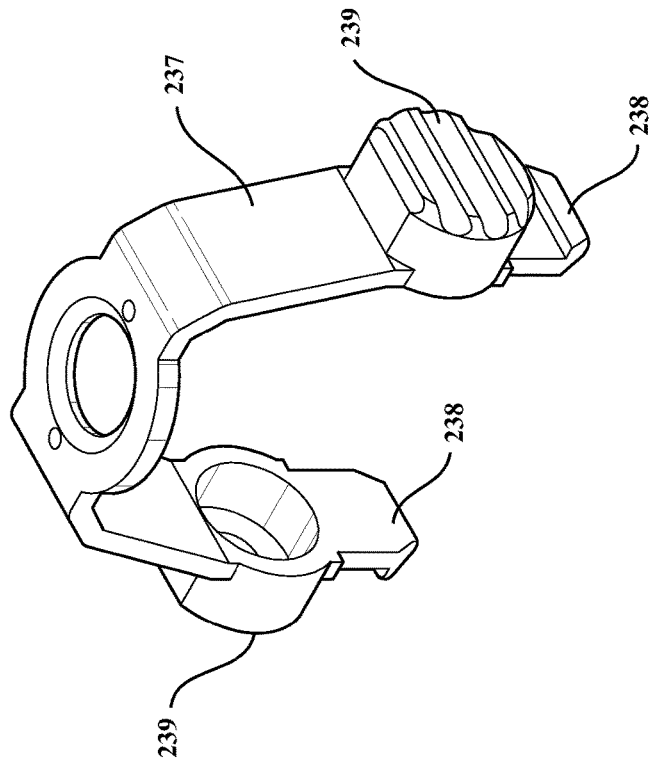
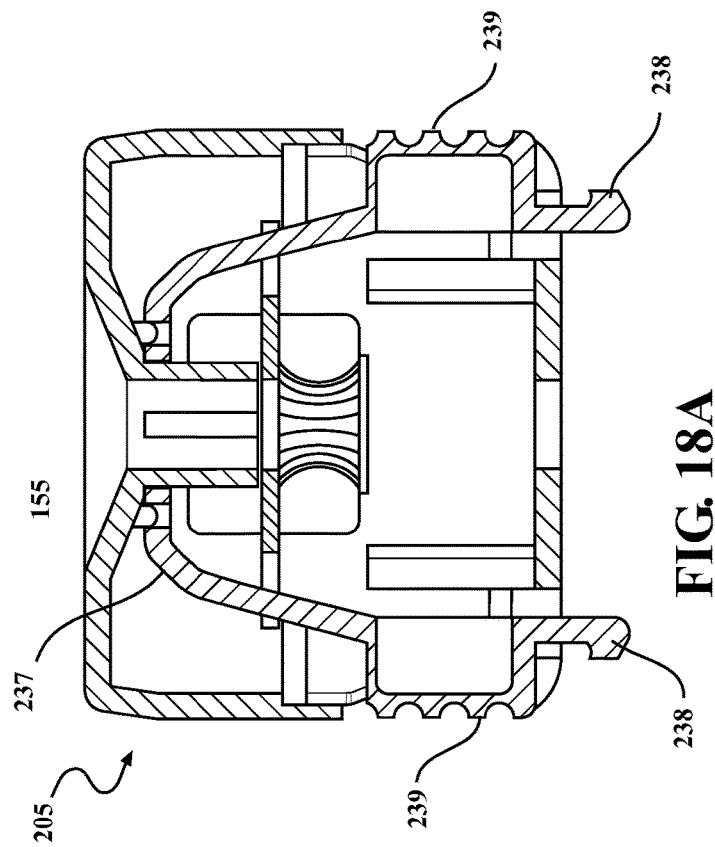
FIG. 18D
FIG. 18A

SCANNING CANNULA

CROSS-REFERENCE TO RELATED APPLICATIONS

This application is a continuation-in-part of U.S. patent application Ser. No. 13/127,577, filed on May 4, 2011, based on PCT Application Ser. No. PCT/US2009/064185, filed Nov. 12, 2009, which claims priority to U.S. Provisional Application Ser. No. 61/116,395, filed on Nov. 20, 2008.

TECHNICAL FIELD

This invention relates to electrosurgery, and more particularly to cannulas for use in electrosurgery.

BACKGROUND

Electrosurgery (ES) and specifically endoscopic ES (EES) are fast growing technologies that expanded a surgeon's capabilities to cut, coagulate, and cauterize tissue and vessels with unprecedented efficiency.

However, ES involves the application of high voltage to the working elements of ES devices such as monopolar hand instruments. Thus, the danger of undesired electrocution and even severe burns always exists and great efforts have been devoted towards implementing durable insulation and protective means, to protect both the surgeon and the patient.

SUMMARY

The present invention provides a scanning cannula for the detection of defects in the electrical insulation of endoscopic ES devices. The scanning cannula has scanning capabilities for detecting arcing and leakage currents through the ES device when the ES device is inserted through the cannula. The present invention thereby adds an active safety measure to electrosurgery, specifically the checking of all devices upon insertion through the scanning cannula.

Further, the present invention provides the means to scan all sterile RF surgical devices upon entry into the endoscopic cannula when it is attached to the patients body, without jeopardizing the devices' sterility, as the scanning cannula is sterile and preferably disposable. Until now, such scanning was not feasible as arcing detection devices are not sterile and require post sterilization to the scanning. It is well known in the MIS industry that defects to insulation can and do occur during the sterilization process in many cases. The current invention provides scanning as last step prior to entry into the body's cavity.

The present invention provides a scanning cannula or an attachable scanning chamber device for the detection of defects in the electrical insulation of endoscopic ES devices. In the case of the attachable scanning chamber version, the device may be attached to commercially available inert (i.e., non-scanning) cannulas. The scanning cannula has scanning capabilities for detecting arcing and leakage currents through the ES device when the ES device is inserted through the cannula. The present invention thereby adds an active safety measure to electrosurgery, specifically the checking of all devices to be used on the patient upon insertion through the scanning cannula.

In one embodiment, the present invention provides a stand-alone scanning cannula that scans mostly tubular insulated elements, typically the working shafts of RF electrosurgical monopolar and hybrid instruments (i.e., RF devices capable of mono-bipolar energy modes), for insulation imperfections and leakage current by communicating via wires or wirelessly with a wired or wirelessly controlled controller or an RF generator having added circuitry necessary to eliminate the controller.

The scanning cannula works with an accompanying controller which includes control and user interface circuits and/or software. The scanning cannula further includes control mechanisms related to the scan cycle. The scanning cannula also may have illumination and insufflation pressure monitoring and even regulating capabilities, thus making it far more valuable than an inert cannula.

A scanning cannula in accordance with the present invention that scans the shafts of electrosurgical instruments for electrical insulation defects includes an elongated sleeve having a receiving end, an opposite exit end directly into the cannula, and a passageway extending from the receiving end to the exit end directly into the cannula. At least one sweeping contact is disposed in the passageway. A communication device is connected to the circuit to transmit signals from the circuit to a controller of a surgical instrument. An electrosurgical instrument inserted into the receiving end of the sleeve passes through the at least one sweeping contact, and any electrical defect of the electrosurgical instrument detected by the at least one sweeping contact is relayed as an error signal to the circuit, which communicates the error signal to the controller. A record of scanning tests and the date and time of each test, whether passed or failed, may also be stored in the controller for future reference.

In one embodiment, each sweeping contact may be a disk-shaped ring including a plurality of fingers extending towards a hollow center of the ring or fingers that extend down from a hollow center in one direction or the other. Other embodiments have additional options for configurations of sweeping contacts, or even just one sweeping contact. The scanning cannula may include a pair of sweeping contacts spatially disposed from each other in the passageway. The communication device may include an antenna that wirelessly transmits signals to the controller. Alternatively, the communication device may include a cable that electrically transmits signals to the controller. The circuit may include a battery that powers the scanning cannula. The circuit may include a capacitor electrically connected to each of the at least one sweeping contact. The circuit may include one or more LEDs that display status information. Preferably, however, all circuits would primarily reside in the controller and receive inputs from the scanning cannula.

The scanning cannula may include a photo cell or micro-switch disposed in the passageway upstream of the at least one sweeping contact. The photo cell or micro-switch may be electrically connected to the circuit, and the photo cell or micro-switch may detect the presence of an electrosurgical instrument in the passageway. The scanning cannula may include a light source in communication with an optical fiber disposed along a length of the sleeve to illuminate the sleeve and the internal surroundings. The scanning cannula may include a pressure sensor electrically connected to the circuit, and a conduit in fluid communication with the pressure sensor for dynamic monitoring of insufflation pressure.

A method of scanning an electrosurgical instrument for electrical defects in accordance with the present invention includes the steps of providing an elongated device which is configured to be disposed in a patient, which has a receiving end, an opposite exit end, and a passageway extending from the receiving end to the exit end; disposing at least one sweeping contact in the passageway; having a circuit in the device; electrically connecting at least one sweeping contact in the device a circuit; connecting a communication device to the circuit to transmit signals from the circuit to a controller of a surgical instrument; inserting an electrosurgical instrument into the receiving end of the sleeve; passing the electrosurgical instrument through the at least one sweeping contact, whereby any electrical defect of the electrosurgical instrument detected by the at least one sweeping contact is relayed as an error signal to the circuit; and communicating the error signal to the controller.

An electrosurgical system in accordance with the present invention for scanning an electrosurgical instrument for electrical defects includes a scanning cannula including: an elongated sleeve having a receiving end, an opposite exit end, and a passageway extending from the receiving end to the exit end; at least one sweeping contact disposed in the passageway; a circuit mounted in the sleeve, the at least one sweeping contact being electrically connected to the circuit; and a communication device (wired or wireless) connected to the circuit to transmit signals from the circuit. A controller is in communication with the scanning cannula. An electrosurgical generator is electrically connected to the controller. An electrosurgical instrument is electrically connected to the controller. The electrosurgical instrument is inserted into the receiving end of the sleeve and passes through the at least one sweeping contact. Any electrical insulation defect of the electrosurgical instrument detected by the at least one sweeping contact is relayed as an error signal to the circuit, which communicates the error signal to the controller. Records of scanning tests and the date and time of these tests, whether passed or failed, may be stored in the controller for future reference.

Optionally, the communication device may include an antenna, and the circuit may wirelessly communicate with the controller via the antenna. Alternatively, the communication device may include a cable that is electrically connected to the circuit and the controller, and the circuit may communicate with the controller through the cable. Upon receiving an error signal from the scanning cannula, the controller may warn the user by displaying a warning message and/or sounding an alarm tone. The electrosurgical device is disconnected from the electrosurgical generator during testing and is only reconnected if the test is successful or an override command (pressing the override button) is provided.

The present invention provides a scanning cannula and controller for automatic scanning of mostly tubular endoscopic electrosurgical devices. This scanning cannula has capabilities for detecting arcing and leakage currents from the electrosurgical device when said device's shaft is inserted through the cannula into the endoscopic surgical site. An active safety measure is added to ES, specifically the checking of all devices upon insertion through the scanning cannula while the scanning cannula is already disposed in the patient's body as the access port to the laparoscopic cavity. The system is set up to only allow surgery to proceed if the instrument has been proven free of defects, or if the surgeon elects to override the safety features of the cannula.

The scanning cannula is connected to an electrosurgical generator via a controller which houses a microprocessor that provides logical control of the scanning process. The controller also contains a high voltage power supply with voltage in excess of that typically selected for ES, thereby eliminating the need for the surgeon to alter the generator settings during testing. The controller also contains high voltage relays that electrically isolate the instrument and the ground pad from the generator unless the test has been passed or the override has been activated. During the test, the instrument is disconnected from the generator to fully isolate the patient from any stray arcing or leakage current. Optionally, the ground pad may also be electrically disconnected from the generator during the scanning process, thereby further isolating the patient from the generator. Once an instrument has successfully passed the test for insulation defects, both the instrument and the ground pad are reconnected to the generator so that surgery may proceed.

In an alternative embodiment, the ground pad is not disconnected during testing, and is not connected to the controller, but instead is connected directly to the generator. In this alternative embodiment then only the instrument would need to be reconnected to the generator in that embodiment so that surgery may proceed.

Scanning of the instrument is performed by two or more sensors contained within the cannula:
  A micro switch or photo-cell to determine the presence of an instrument within the cannula.
  A high-voltage sweeping contact to scan for insulation defects.

A low voltage sweeping contact may also be used in some embodiments to determine the position of the instrument in the cannula. Specifically, the low voltage contact may be used to sense whether the exposed tip region or the insulated shaft of the instrument are currently being scanned by the high voltage contact.

Outputs from these instruments are used by the microprocessor in the controller to determine whether the instrument has passed testing. The controller is fitted with an LCD screen (or a different display) and audio sounds to inform and alert the user of the results of the scanning test.

These and other features and advantages of the invention will be more fully understood from the following detailed description of the invention taken together with the accompanying drawings.

BRIEF DESCRIPTION OF THE DRAWINGS

In the drawings:

FIG. 10 shows an elevational view of the scanning cannula and trocar and FIG. 10A is an enlarged section through the scanning cannula head and the attached trocar;

FIG. 13 shows a typical application of an attachable/detachable scanning head with dual sweeping contacts to be attached to a conventional cannula;

FIG. 13A shows the cable secured to the scanning head that attaches the scanning head to a controller;

FIGS. 18A, 18B, 18C and 18D show an attachable scanning head with a single sweeping contact (and the attachment clip shown separately at FIG. 18D) to be attached to commercially available cannulas;

FIGS. 20, 20A and 20B illustrate user interfaces for communication with the user as well as the hand operated override control on the scanning cannula.

DETAILED DESCRIPTION OF THE INVENTION

Figure 1:
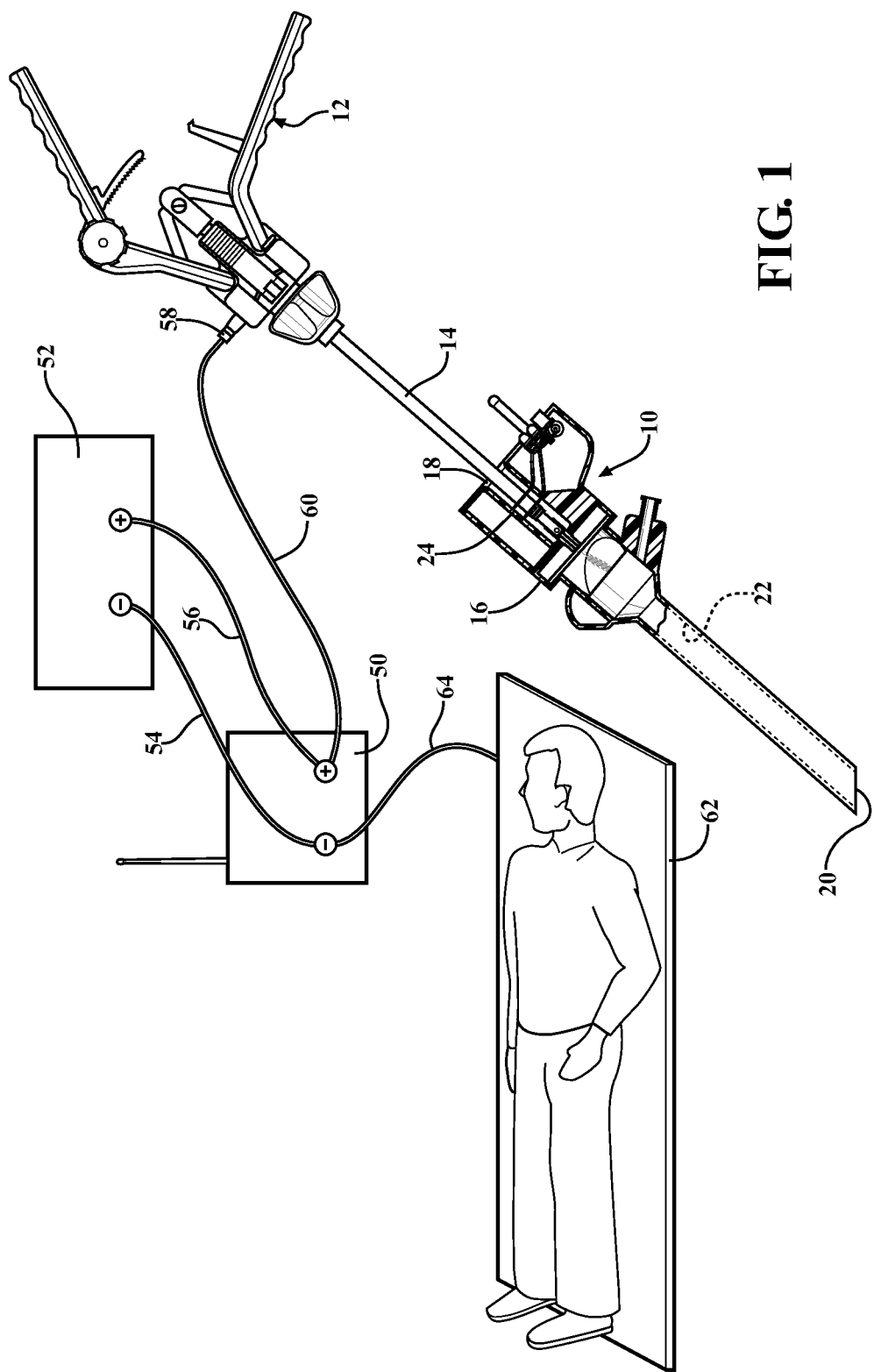
FIG. 1 is an environmental view of a wireless scanning cannula in accordance with the invention having an electrosurgical instrument inserted therein.

Referring now to the drawings in detail, numeral 10 generally indicates a scanning cannula in accordance with the invention. The scanning cannula 10 provides for scanning of an electrosurgical instrument and detection of defects in the electrical insulation of the instrument, which increases the safety of the instrument and related electrosurgical procedures.

Figure 2:
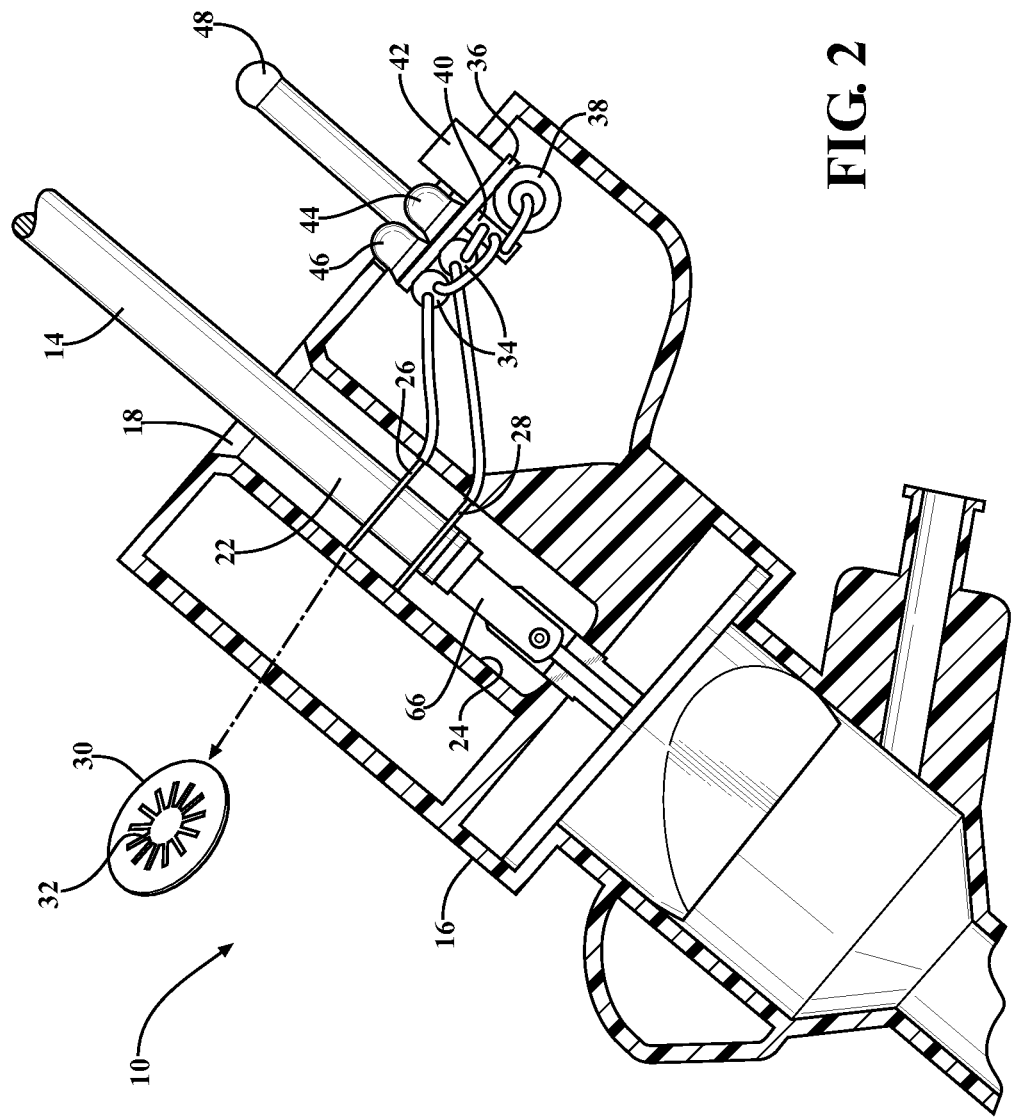
FIG. 2 is an enlarged view of a portion of the wireless scanning cannula.
Figure 3:
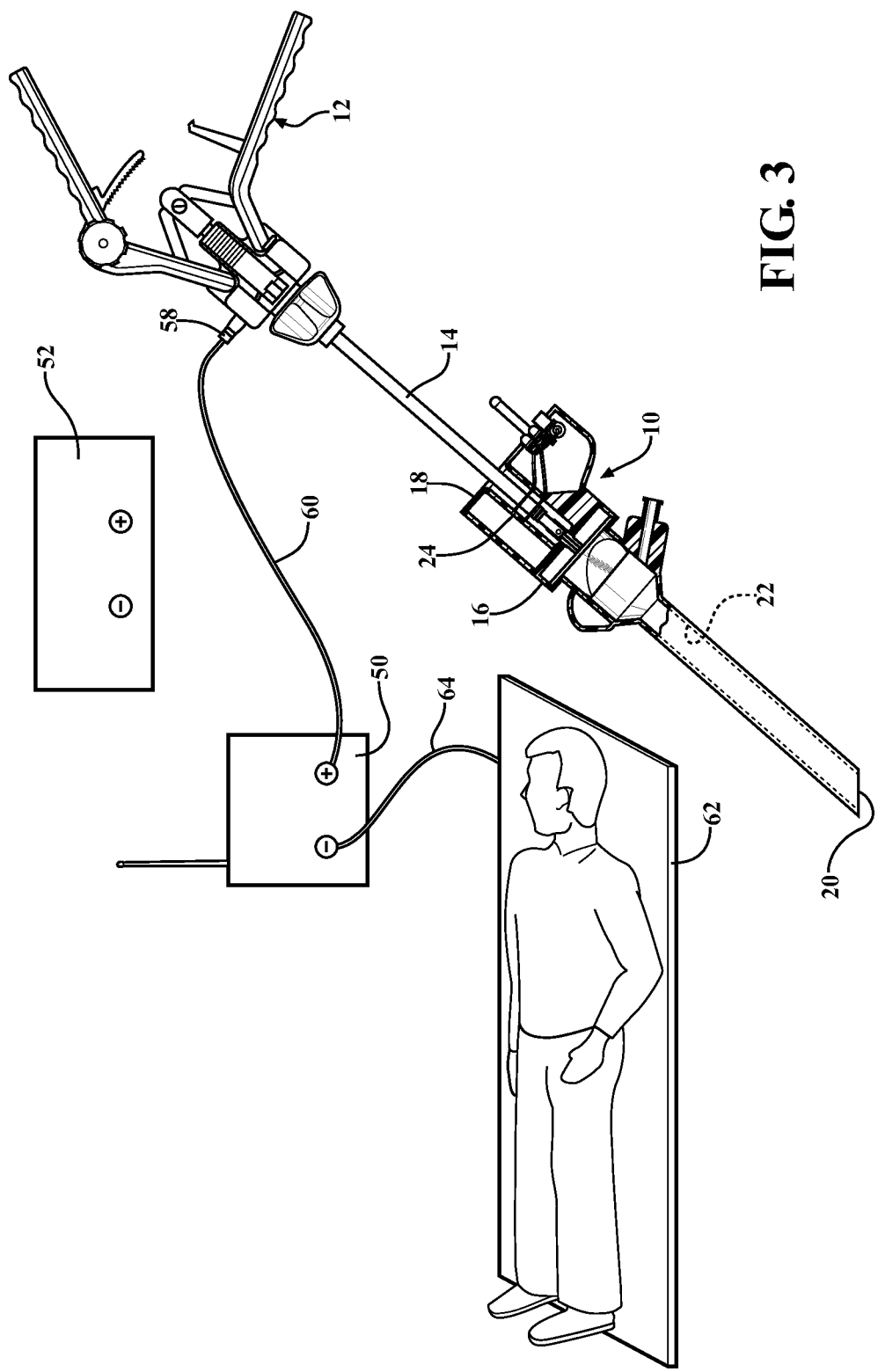
FIG. 3 is an environmental view of the wireless scanning cannula and its related circuit in scanning mode.

As illustrated in FIGS. 1 through 3, an endoscopic, monopolar (RF) surgical device 12 such as an electrosurgical instrument having an insulated shaft 14 is partially inserted into the scanning cannula 10. The insulated shaft 14 of the surgical device 12 is scanned for insulation defects by the scanning cannula 10 as described herein.

The scanning cannula 10 includes an elongated sleeve 16 having an instrument receiving end 18, an opposite exit end 20, and a passageway 22 extending from the receiving end to the exit end. A portion of the passageway 22 adjacent the receiving end 18 defines a scanning chamber 24. Two sweeping contacts 26, 28 are disposed in the scanning chamber 24 and are spaced apart at a safe distance to avoid arcing between them (e.g., between 1 mm and 8 mm). Each sweeping contact 26, 28 may be a disk-shaped ring 30 including a plurality of fingers 32 extending towards a hollow center of the ring. A circuit such as a printed circuit board (PCB) 36 or similar circuit arrangement is mounted in or on or integral with the sleeve 16. The sweeping contacts 26, 28 are each separately wired to a capacitor 34 included in the PCB 36. The PCB 36 includes a battery 38, the two capacitors 34 each electrically connected to a separate sweeping contact 26, 28, a voltage buildup mechanism 40 between the battery 38 and capacitors 34, a control mechanism (activation button 42 such as an on/off switch or similar), two LEDs 44, 46 (although more than two LEDs may be included), and a communication device 48 to transmit signals from the PCB 36. In one embodiment, the communication device 48 may include an antenna that wirelessly transmits necessary signals from the PCB 36 to a wireless controller 50 that is electrically connected to the surgical device 12.

FIG. 1 illustrates "normal" wiring for the wireless version of the scanning cannula as to be used in surgery. The wirelessly controlled controller 50 is connected to monopolar and ground ports on an electrosurgical generator 52 via cables 54, 56. The surgical device 12 is wired to the monopolar port on the controller 50 via a power plug 58 and cable 60. A ground pad 62, which is attached to a patient, is connected as shown to the controller 50 ground via a cable 64, but may also alternatively be connected directly to the generator's ground.

FIG. 2 illustrates a typical situation pertaining to a scanning function of the scanning cannula 10. In a scanning mode, activation button 42 is depressed (switched to the on position), and the battery 38 charges the capacitors 34 and sweeping contacts 26, 28 with high voltage. At the same time, antenna 48 transmits a signal to the controller 50 to switch the circuits as shown in FIG. 3.

When the capacitors 34 are charged, blue LED 46 indicates that the scanning cannula 10 is ready for a scanning procedure.

A practitioner such as a surgeon or other health care provider inserts the shaft 14 of the surgical device 12 into the scanning chamber 24 through the receiving end 18 of sleeve 16. The scanning then proceeds as follows. Exposed jaw assembly 66, at a distal end of the insulated shaft 14, is inserted through a tubular inlet (at receiving end 18) of the scanning chamber 24 and moved through the charged sweeping contacts 26, 28. The initial passage of the exposed jaw assembly portion 66 is detected by arcing or conduction from sweeping contacts 26 and 28 onto the exposed jaw portion 66. The arcing may be limited by a resistive circuit designed to reduce current flow upon arcing. The upper contact is typically set to 3000V or more and the lower contact is set to a low voltage such as 5V. Once the lower sweeping contact has returned to its lower setting (5V) and is no longer detecting the exposed metallic tip of the instrument, the scanning of the shaft begins. Any further arcing from sweeping contact 26 is identified as a defect in insulation. The signal leads to a warning on either or both of the scanning cannula 10 and the controller 50, and eventually to the cutting of power from the generator 52 to the surgical device 12 upon completion of the scanning. The scan itself, if executed automatically, is limited in time to approximately 5 seconds, as an example. After the scan, if no arcing was detected during the scan period, an OK signal appears on both the scanning cannula 10 and the controller 50. In one embodiment, the scan duration and scan initiation may be controlled manually by switching the controller 50 to scan mode and switching the controller 50 back to normal work mode once the surgical device 12 has been inserted and no alarm was displayed.

Figure 4:
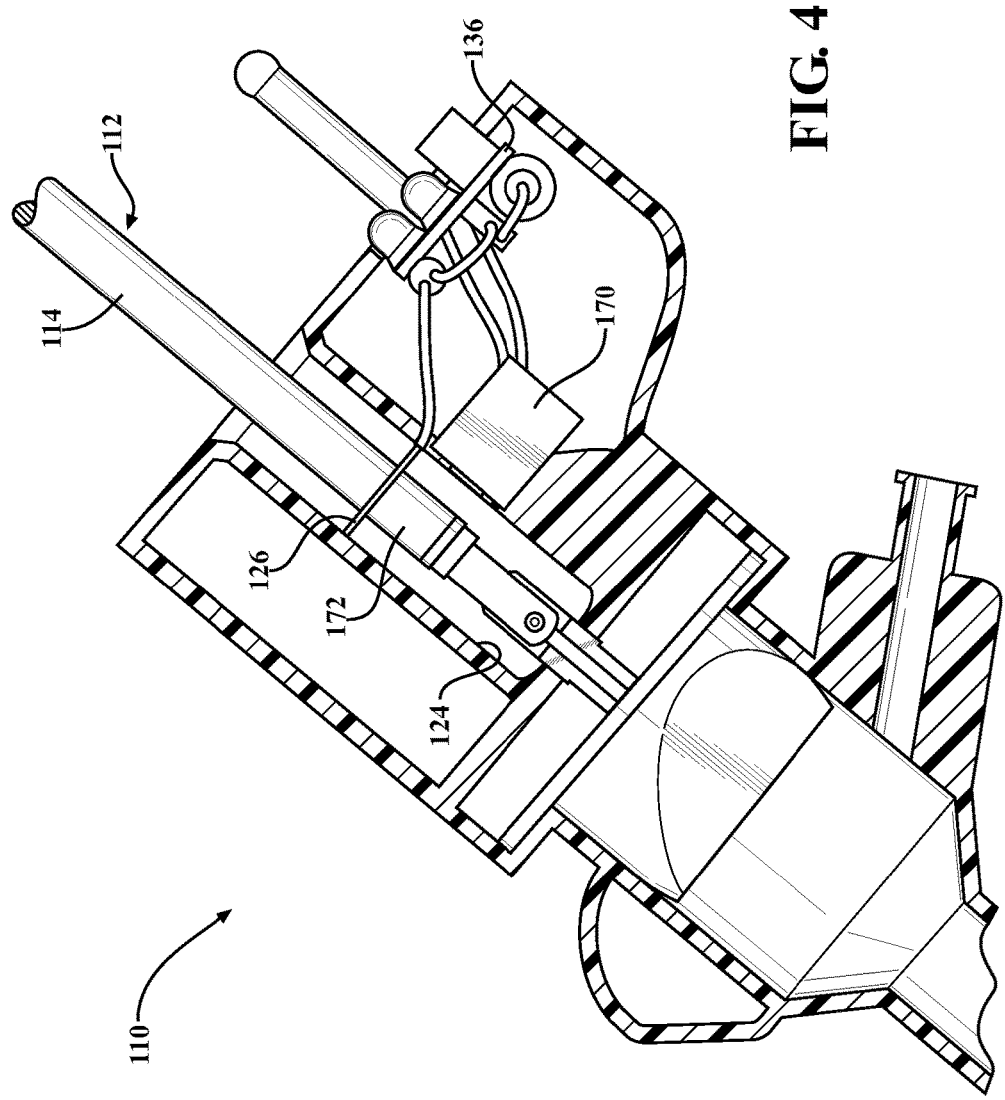
FIG. 4 is a partial view of an alternative embodiment of a scanning cannula in accordance with the invention.

FIG. 4 illustrates another embodiment of detection at the beginning of the scanning procedure. In this embodiment, the scanning cannula 110 includes one sweeping contact 126. A photo or light cell 170 is disposed below (downstream of) the single sweeping contact 126 in the scanning chamber 124. The photo cell 170 is electrically connected to the PCB 136. The photo cell 170 may detect the presence of the dark insulating sheath 172 of the shaft 114, indicating the PCB that the surgical device 112 is present in the scanning chamber 124. Any further arcing from the single sweeping contact 126 is then processed by the PCB 136 as evidence of an insulation defect.

Figure 5:
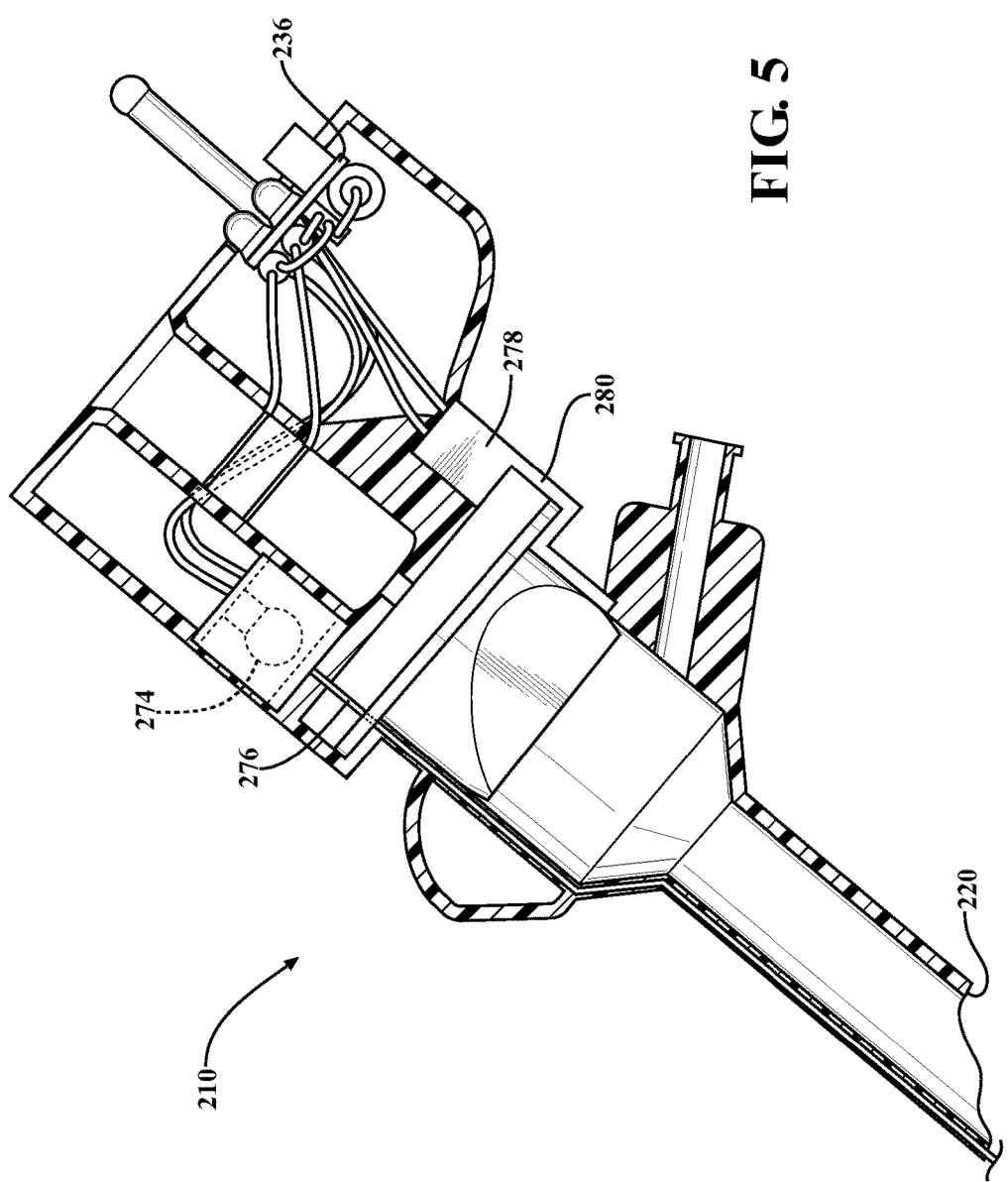
FIG. 5 is a partial view of another alternative embodiment of a scanning cannula in accordance with the invention.

In yet another embodiment illustrated in FIG. 5, the scanning cannula 210 may optionally include a light source 274 such as a bulb or similar that emits light which is then transmitted via optical fibers 276 or other transmission means such as a built-in light conduit or similar. Light from the light source 274 glows through the distal tubular exit end 220 of the scanning cannula 210, to aid in illumination when needed and traceability during the penetration stage. The scanning cannula 210 may also include dynamic pressure monitoring of insufflation pressure. A pressure sensor 278 may read cannula/insufflation pressure via conduit 280. The scanning cannula may even control an insufflator (not shown) remotely. The light source 274 and pressure sensor 278 may each be electrically connected to the PCB 236.

Figure 6:
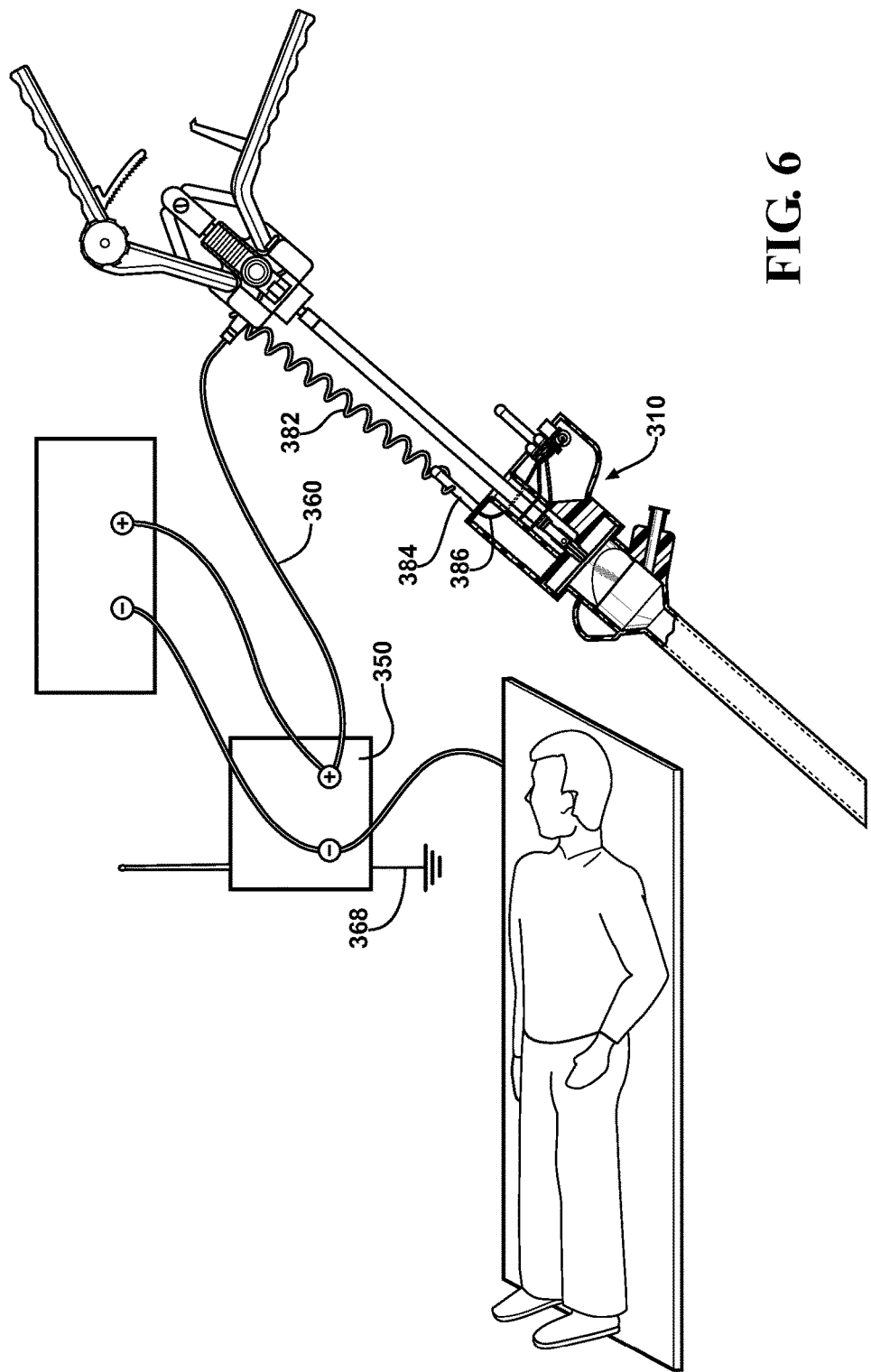
FIG. 6 is an environmental view of yet another alternative embodiment of a scanning cannula in accordance with the invention as a wired embodiment.

In an alternative embodiment shown in FIG. 6, the scanning cannula 310 may be arranged in wired form, i.e., using a powered, multi-channel cable from the controller 350 into the scanning cannula 310 and eliminating the battery and capacitors in the PCB. An example is illustrated in FIG. 6, in which powered cable 382, branched from cable 360, is connected with the scanning cannula 310 circuitry via power plug 384 and wires 386. The cable 382 could, alternatively, be attached directly to the controller 350. Wireless communication is therefore not required as the physical connection (i.e., cable) with the controller 350, directly or through branching, may be used to convey information such as test mode beginning, test mode end, and scanning results. A decision to cut off power to the electrosurgical generator 352 may be made in the controller 350 or the generator 140, if equipped properly. Optionally, another ground reference may be achieved by having the controller 350 include an attached ground wire 368, thus avoiding the use of patient capacitance as the ground reference.

The description herein will demonstrate the details of the invention. The invention provides a means to scan for insulation defects of incoming devices into the scanning cannula and disconnect the RF power source (i.e. the generator) from a defective device and thus eliminating potential injuries to patients and users.

Figures 7, 7A:
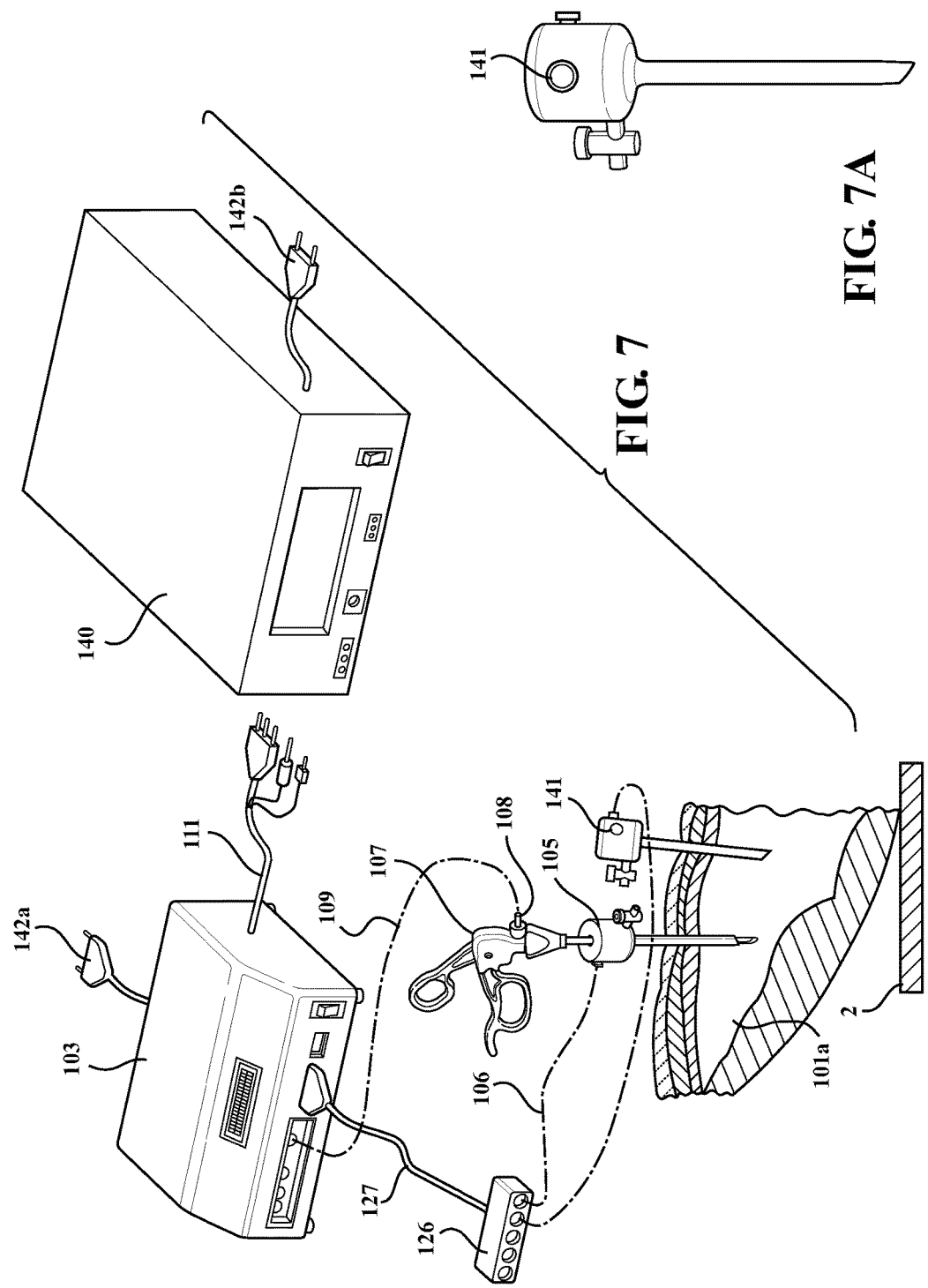
FIG. 7 shows a typical setup for MIS (Minimally Invasive Surgery) with a wired scanning cannula, controller, generator, patient (a portion in cross-section), ground pad, and wiring.
FIG. 7A shows a wired scanning cannula that can be used with the setup of FIG. 7.

FIG. 7 shows a typical setup for minimally invasive surgery, involving the scanning cannula and the controller. The patient 101 is on the operating table similar to FIG. 1 (patient shown here in partial section), is anesthetized and is connected to a ground pad 2 connected to the controller 103 via cable 4 (not shown) also as similar to FIG. 1. Ground pad 2 may be connected directly into the generator 140 ground as an alternative. A scanning cannula 105 is affixed to the patient's abdominal wall and is wired to the controller via cable 106. In a case where a plurality of scanning cannulas are being used, the cable 106 may be connected first into a multiple connector 126 that connects into the controller 103 via cable 127.

An insulated monopolar surgical instrument 107 is inserted into the laparoscopic cavity 101a via scanning cannula 105. The instrument 107 is hooked to the controller 103 via its power plug 108 and cable 109. The controller 103 is hooked to the generator (ESU) 140 via cable 111. The controller is connected to a standard wall socket via cable 142a. The ESU is connected to a standard wall socket via cable 142b. Also included in FIG. 7 is a second scanning cannula 141 which is inserted into the body of the same patient (human, animal, etc.). Scanning cannula 141 can operate the same as scanning cannula 105 or can be wirelessly connected to a controller as illustrated above in FIGS. 2 through 6. The scanning cannula is also illustrated separately in FIG. 7A.

Figure 8A:
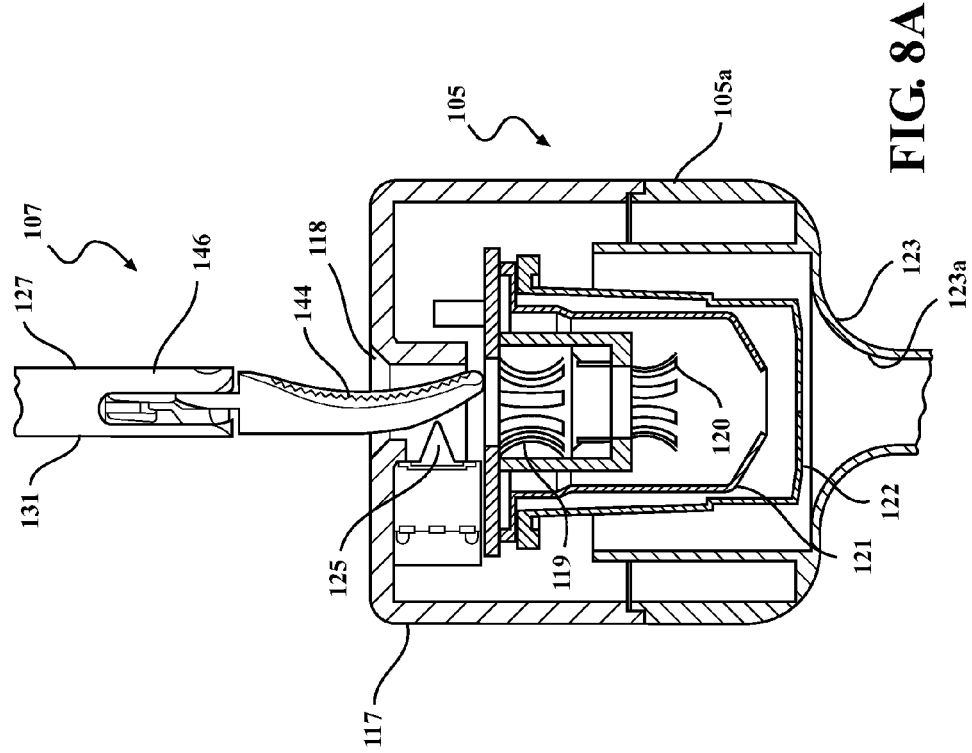
FIG. 8A is an enlarged sectional view of the head portion of the scanning cannula with a monopolar instrument partially inserted.
Figure 8:
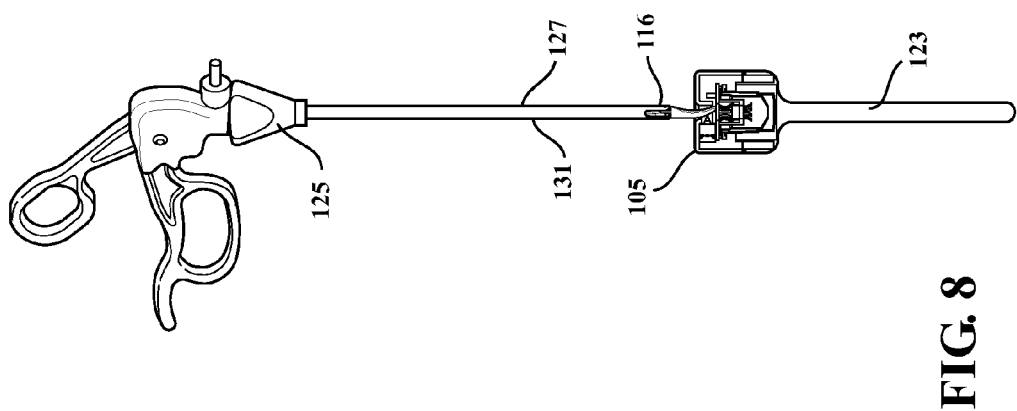
FIG. 8 shows a view of the scanning cannula with advanced sweeping contacts and a cross section through the scanning portion.
Figure 9:
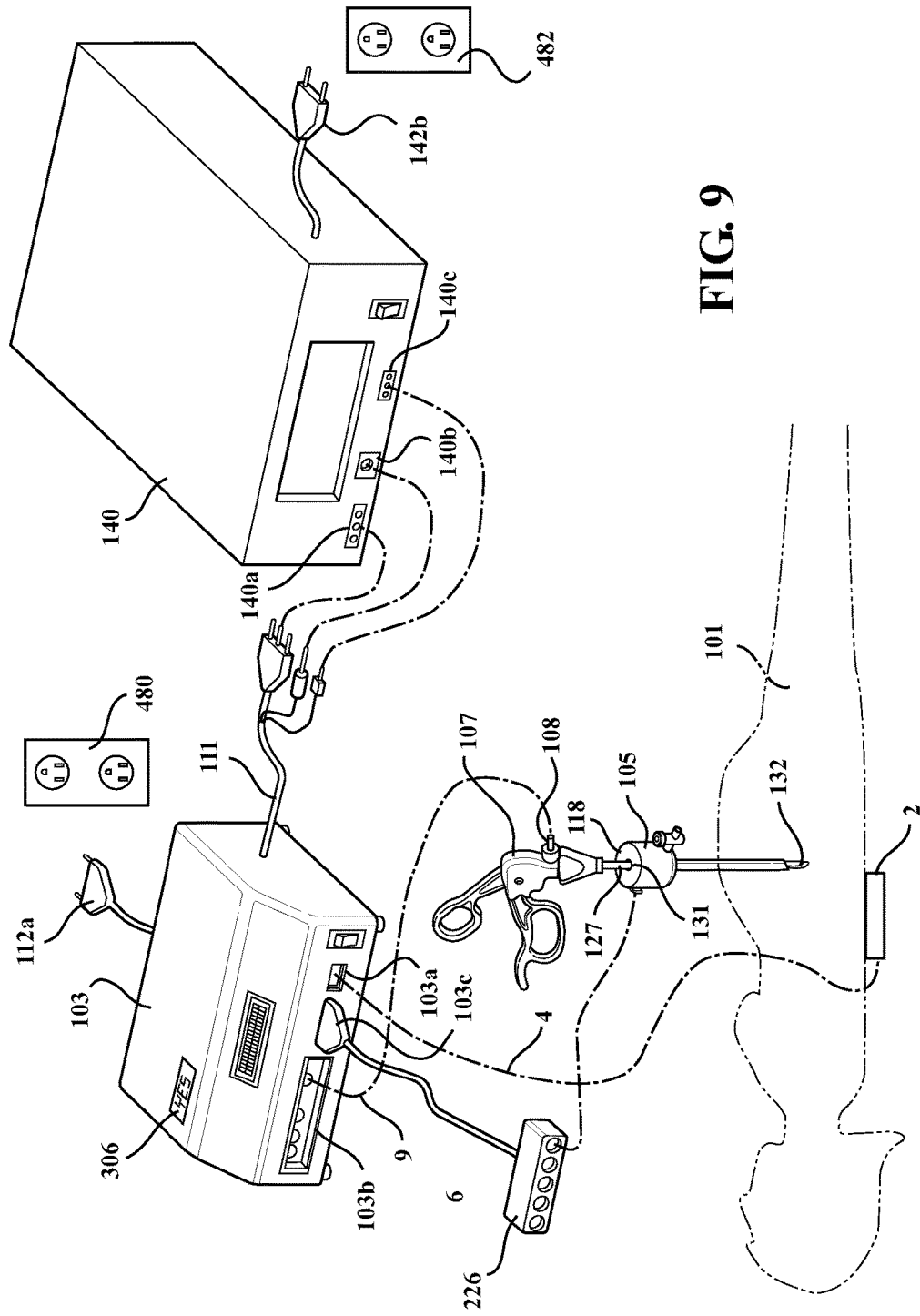
FIG. 9 shows a typical monopolar instrument entering the scanning cannula.

FIGS. 8 and 9 show a typical view of a scanning cannula 105 schematically inserted in the patient and, at FIG. 8A, a partially inserted monopolar instrument shaft 127 just prior to insertion into the abdominal wall. FIG. 8A is a cross section through the upper portion of scanning cannula 105. We will focus on the scanning features of the scanning cannula and describe the general features of the monopolar instrument 107 and the cannula portion 123 of the scanning cannula 105 for clarification only.

The monopolar instrument shaft 127 is inserted into the scanning cannula 105. The instrument clevis 146 is rigidly attached to the monopolar instrument shaft 127 and pivotally to the monopolar instrument jaws 144. The monopolar instrument shaft 127 passes through the scanning cannula 105 at cover 117 via tapered inlet 118 where it trips limit switch 125, and then through upper sweeping contact (USC) 119 and lower sweeping contact (LSC) 120. The monopolar instrument shaft 127 extends through radial seal 121 and through duckbill seal 122 to enter the scanning cannula hollow shaft 123 at its interior 123a. The monopolar instrument shaft 127 is made long enough so it protrudes through the hollow shaft 125 enough to expose its clevis 146 and jaws 144.

FIG. 9 shows a typical monopolar surgical instrument 107 inserted into a scanning cannula 105 via inlet 118. Upon entering the scanning cannula 105, the exposed jaws first touch (and trip) the micro-switch 125, then touch the USC 119, and lastly touch the LSC 120 (see FIG. 11). These occurrences are communicated to and noted by circuitry in the controller and are followed by the scanning of the insulated portion 131 of the shaft 127. The shaft 127 of the instrument 107 has an insulated portion 131 (see FIGS. 8 and 8A) that will be fed through the hollow shaft 123 until reaching the bottom of the abdominal cavity and scanned at the same time by the USC 119 and LSC 120 as per the steps below:

Preparation Stage

With reference to FIG. 9:
Patient on operating table, anesthetized with ground pad attached.
Controller (CB) 103 is attached to wall socket 480 via cable 112a. CB 103 is ON.
Patient insufflated and the scanning cannula 105 together with the trocar 145 (FIG. 10) is disposed into patient's abdominal wall.
Trocar 145 (FIGS. 10 and 11A) is removed
Electrosurgical generator (ESU) 140 is ON. Surgeon selects desired settings Controller (CB) 103 is placed conveniently between patient and ESU 140

CB 103 side, permanent cable 111 (3 branches) is attached to ESU 140 monopolar outlets 140*a* and 140*b*, as well as ground pad outlet 140*c*.

Cable 4 of ground pad 2 is connected to CB 103 at outlet 103*a* or alternatively directly to ESU 140 ground pad outlet 140*c*.

Monopolar instrument 107 is connected by its power plug 108 to CB 103 via cable 9 to outlet 103*b*.

Figure 19A:
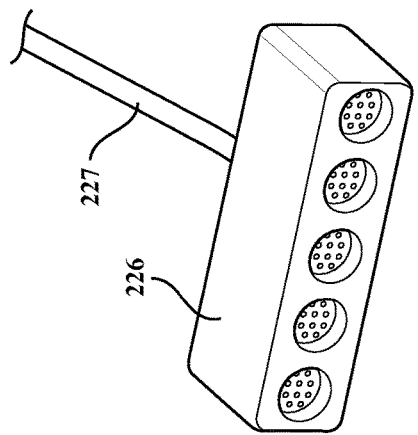
FIG. 19A illustrates an attachment device for implementing multiple scanning cannulas in the operation of one patient.
Figure 19:
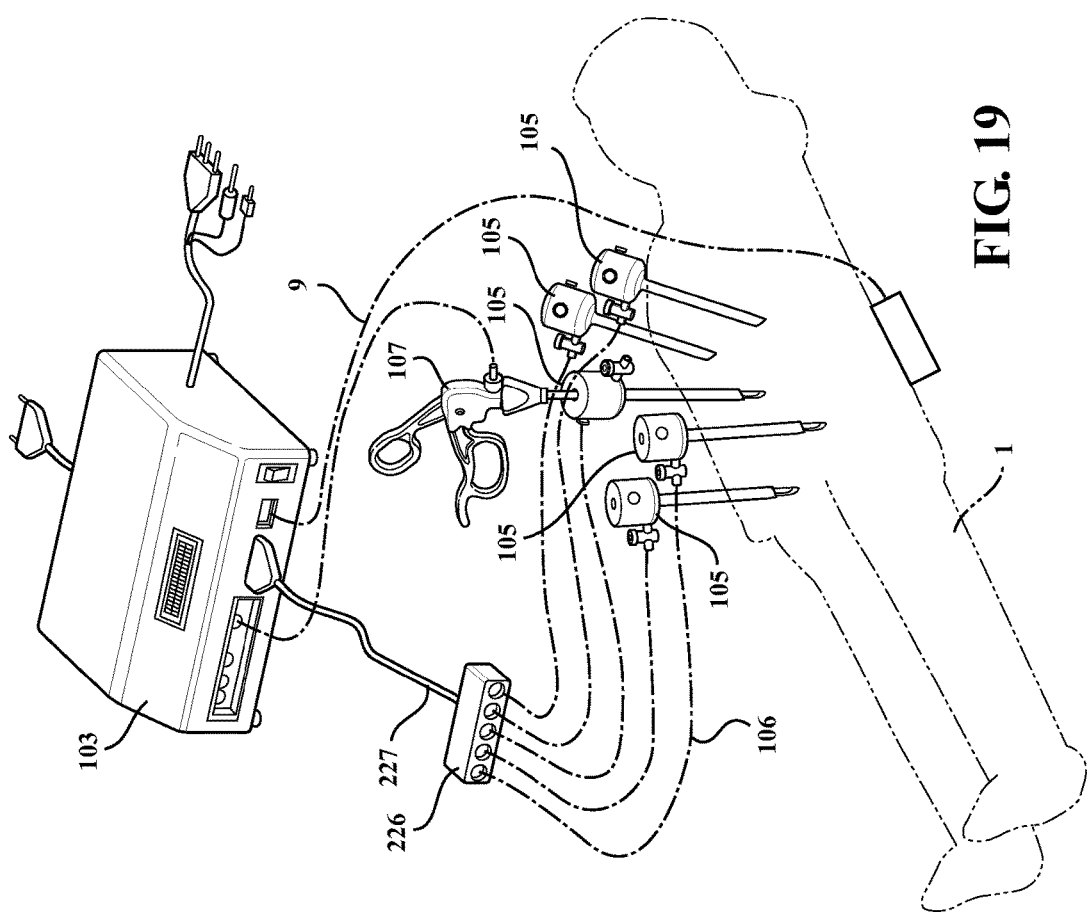
FIG. 19 shows the application of multiple scanning cannulas in the operation on one patient.

Proprietary cable (PC) 6 is permanently connected to SC 105. Its extension is attached to the SB 103 at outlet 103*c* or through multi-connector 226 (FIG. 9 or FIG. 19).

If trocar 145 was not removed or an instrument is inside the SC 105 prior to connecting the SC 105 to the powered CB 103, audio and written messages will appear "Please remove instrument from SC."

During Testing

Whenever the limit switch, micro-switch or photocell indicates that the cannula is empty, the system goes into the following initial state awaiting an instrument so that a test may begin. LSC 120 is initially at 5V. USC 119 is initially at 5V or at 4000V as explained below. Initially and throughout the testing, the instrument is kept at ground potential and the contacts are connected to their respective voltages via individual resistors. The relays electrically disconnect the generator 140 from the instrument power plug 108 and electrically connect the testing circuit ground 470 to the instrument ground plug 108.

In another variant, only LSC 120 is kept at low voltage while USC 119 is at 4000V, or it is instantaneously turned on at the moment USC 119 is ceasing to have contact with the conductive distal tip portion (jaws 144) of the instrument 107. LSC 119 is generally left "ON" at its typical voltage (approximately 5V or low voltage) as it does not affect anything. One alternative could be to turn it "OFF" (or zero volts) when it is not needed.

Surgeon inserts the shaft 127 of an insulated monopolar instrument 107 into SC 105.

SC 105 is ON together with CB 103 before testing.

Tip (jaws 144) of instrument 107 hits micro switch 125 (FIG. 11) that signals CB 103 of an incoming device.

CB 103 announces the presence of an instrument in the cannula 105.

Instrument tip (jaws 144) hits USC 119 (FIG. 8A), causing arcing and/or current flow to occur between it (e.g., 4000V) and the instrument 107 (ground). This is sensed and registered by CB 103, and indicates that the exposed tip region (jaws 144) of the instrument 107 is now in the scanning section of the cannula 105 (in other embodiments USC 119 may be neutral initially or charged at a low voltage, such as 5V).

Instrument tip (jaws 144) hits second sweeping contact LSC 120, causing its voltage to drop to that of the instrument 107. This is sensed and registered by CB 103, and indicates that the exposed tip region (jaws 144) of the instrument 107 is still in the scanning section of the cannula 105. The sequential detection of the tip (jaws 144) first by USC 119 and then LSC 120 provides confirmation that both USC and LSC are working correctly and are not defective or damaged.

As the exposed tip (jaws 144) of the instrument 107 moves beyond LSC 120, the insulated shaft 131 of the instrument touches LSC 120 and therefore the voltage of the LSC 120 is no longer pulled to the ground voltage of the instrument 107. The return of LSC 120 to +5V indicates to the CB 103 that the insulated shaft 131 is touching the contacts and it is time to begin the test. At this point, USC 119 is at a high voltage of approximately 3000V to 4000V and the test for insulation defects begins. LSC 120 is disconnected via a high voltage relay 301. CB 103 announces the beginning of the scanning test. A software based timer within the software of FIG. 14 or a modification thereof is commenced for the allowed test duration (e.g., 5 sec) to allow a reasonable time for the scan to complete.

The surgeon continues to push the instrument 107 deeper into the patient 1 through the cannula 105, allowing the shaft 130 to pass along the sweeping contacts 119 and 120. Any arcing sensed by USC 119 from this moment until the expiration of the Allowed Test Duration triggers an alarm and a message to the surgeon that the instrument is defective. If no arcing is sensed by USC 119 before the timer expires, the instrument is considered defect free. If found to be defective, the instrument 107 must be removed from the cannula 105 before another attempt at passing a test can be made. The generator 140 remains disconnected from the instrument 107 and ground pad 2 until a test is successfully passed, which then may generate a record of the result, and an "OK" sound along with the date and time of the test, and stored in the controller (or another storage device) for future reference.

Any incoming inserted shaft will trigger the same cycle as above.

The use of two sweeping contacts 119 and 120 and a micro-switch 125 allows:
  A. Detection of the presence of an instrument in the scanning cannula.
  B. Confirmation of the operation of the sweeping contacts by their sequential detection of the exposed tip of the instrument.
  C. Detection of the insulated portion 131 of the instrument shaft 127 once the LSC 119 returns to 5V.
  D. Detection of insulation defects in the insulated portion of the instrument via sweeping with high voltage by the USC 120.

Figure 11B:
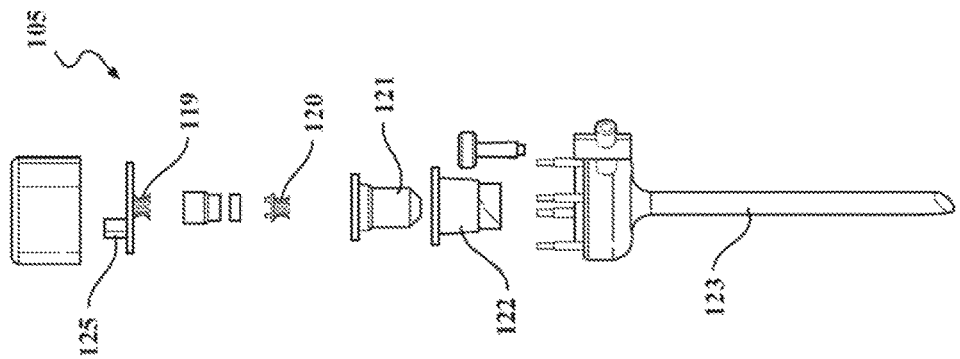
FIG. 11B shows an exploded elevational view of the scanning cannula.
Figure 11A:
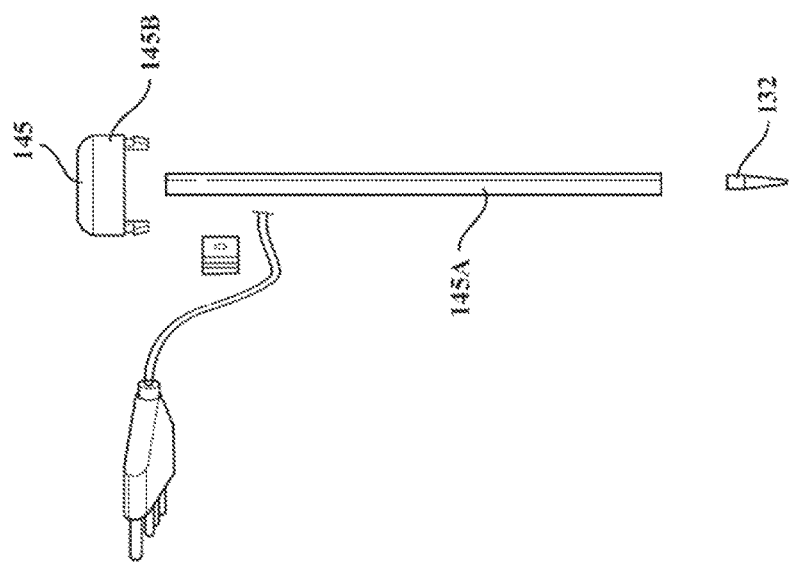
FIG. 11A illustrates a exploded elevational view of a conventional trocar that may be used with the cannula device.

FIGS. 10, 10A, and 11A provide elevational and exploded isometrics of the scanning cannula 105 and the trocar 145, plus an inside view of the scanning elements as situated within the scanning cannula head portion 105*a*. The trocar 145 comprises a cap portion 145B and a shaft 145A having a tip portion 132. The trocar 145 is used, while situated in the scanning cannula 105 to penetrate the abdominal wall of the patient until the scanning cannula is affixed deep enough as per the surgeon's discretion. At that point the trocar 145 is removed, leaving the through channel in the scanning cannula 105 free so that minimally invasive surgical devices can be inserted while protecting the insufflation pressure in the abdominal cavity.

Figure 11:
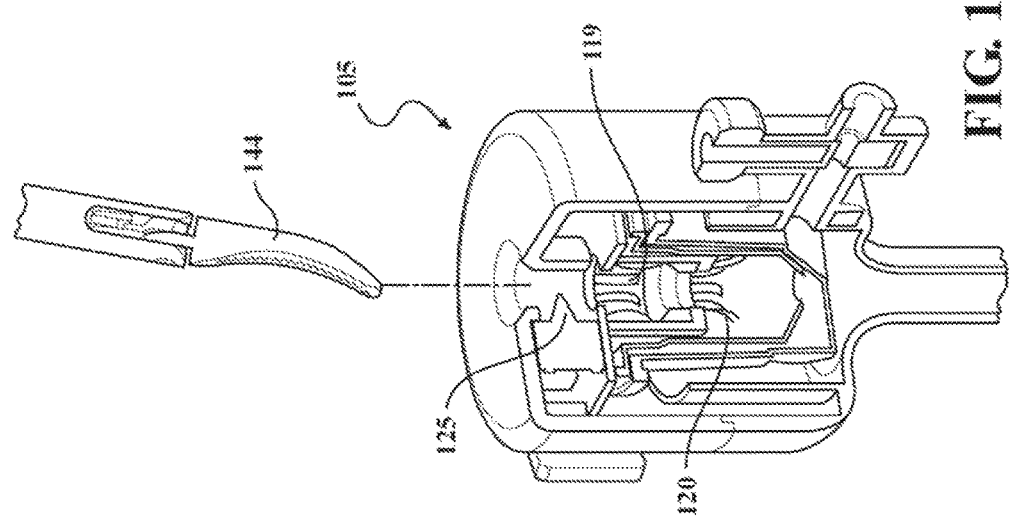
FIG. 11 shows a sectional perspective view of the cannula head.
Figure 12A:
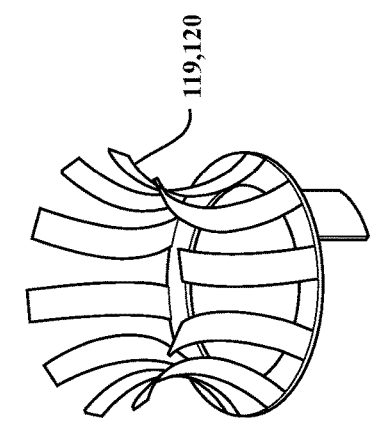
FIGS. 12, 12A, 12B, 12C, 12D, 12E and 12F show details of the sweeping contacts, the micro switch, and a micro switch and contact board assembly.
Figure 12B:
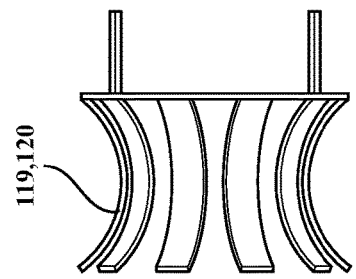
Figure 12C:
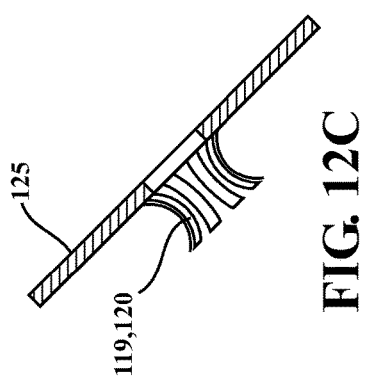
Figure 12D:
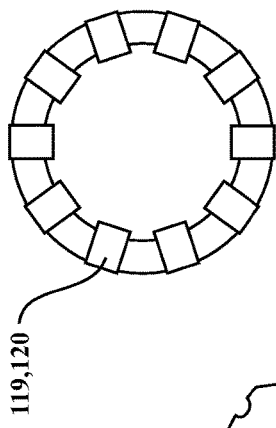
Figure 12:
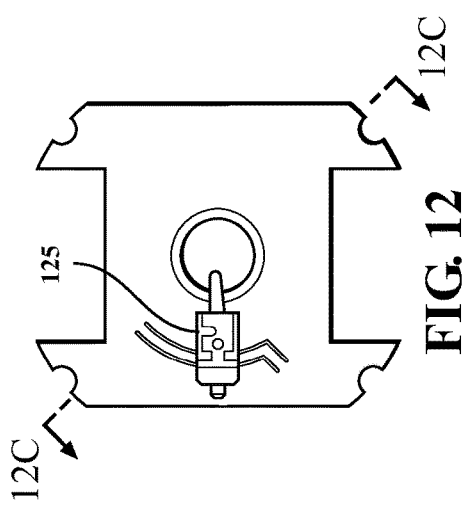
Figure 12F:
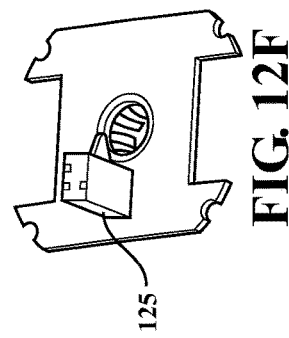
Figure 12E:
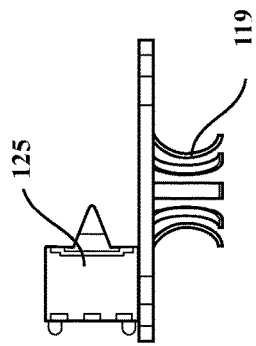
Figure 13C:
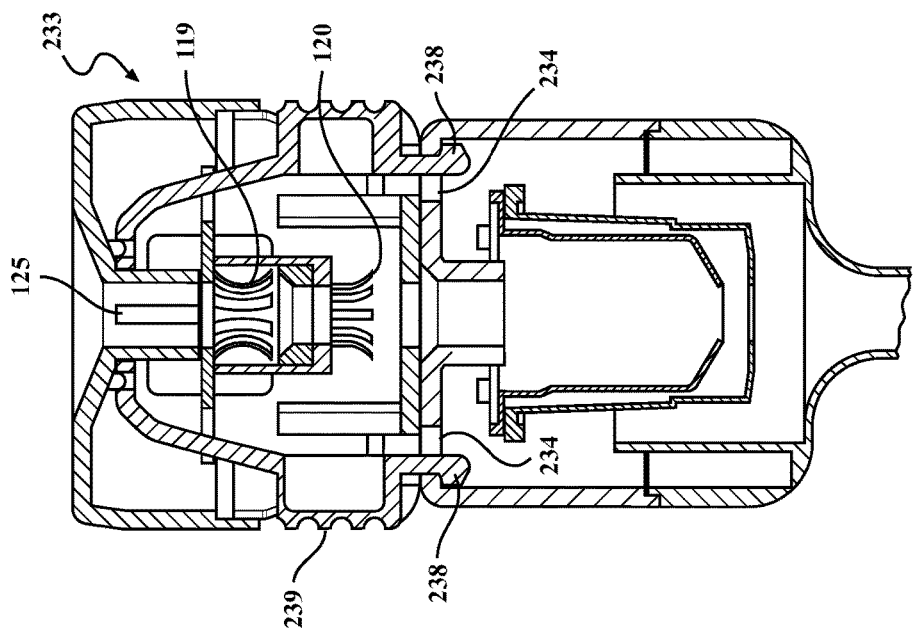
FIGS. 13B and 13C show an elevated perspective view of the scanning head of FIG. 13 detached from the adjacent cannula and a cross-section of the scanning head of FIGS. 13, 13A and 13B attached to the cannula.
Figure 13B:
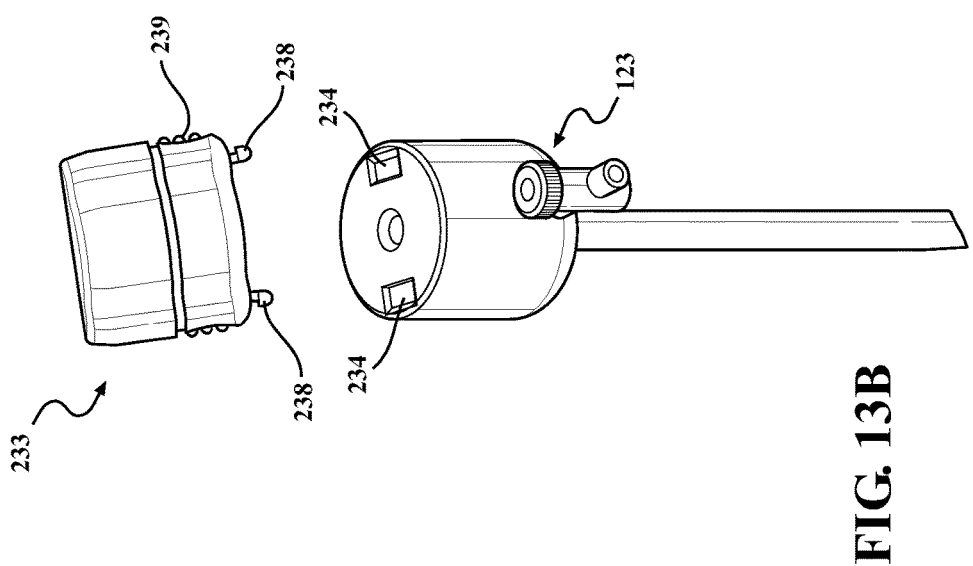

FIGS. 11 through 11 B and 12 through 12F show sweeping contacts 119 and 120, preferably made out of elastic conductor material and FIGS. 11, 11B, 12, 12E and 12F have a typical view of micro-switch 125.

Figure 14:
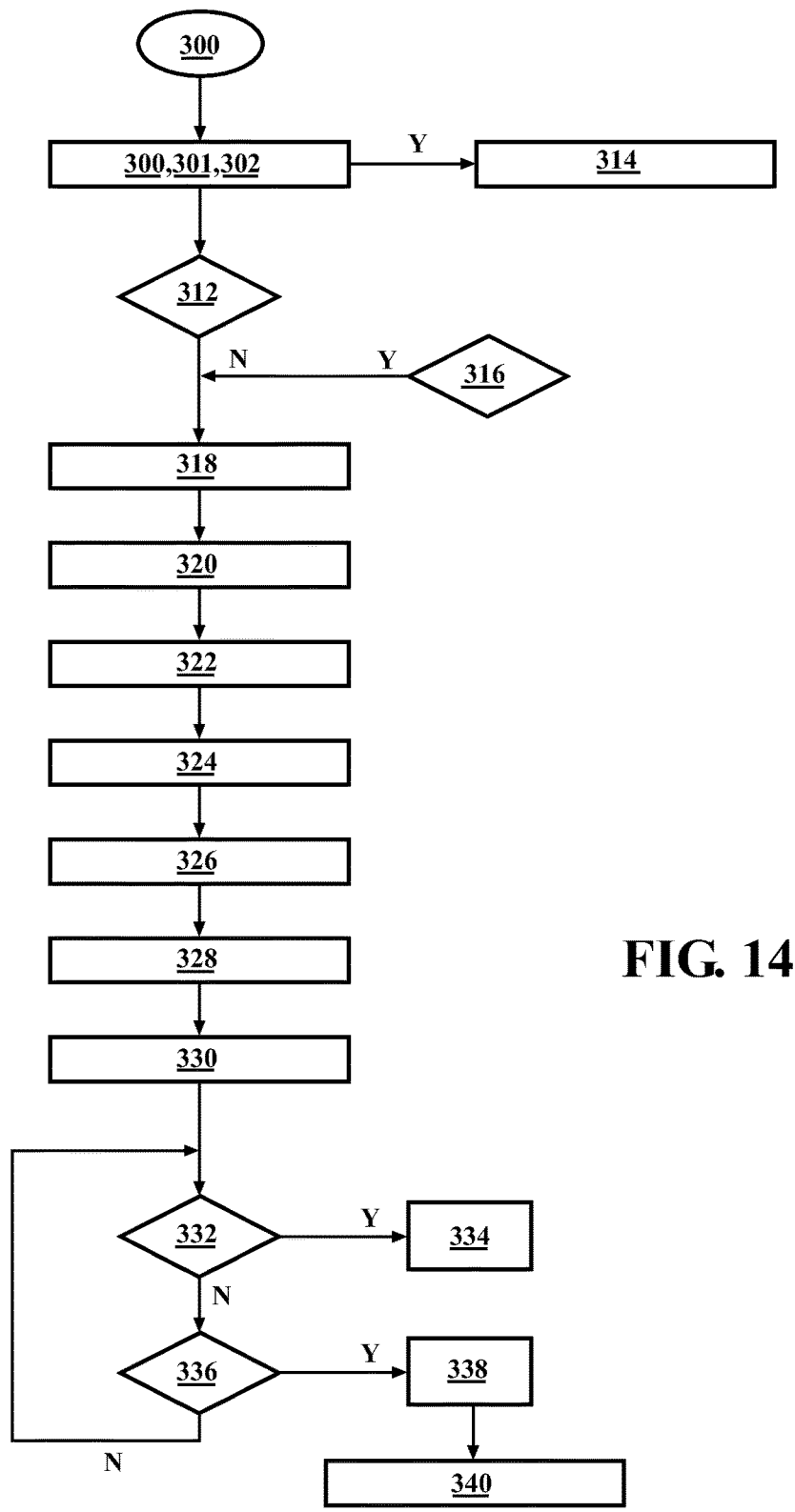
FIG. 14 shows the flow chart for the controller to control at least one scanning cannula having two sweeping contacts.
Figure 15:
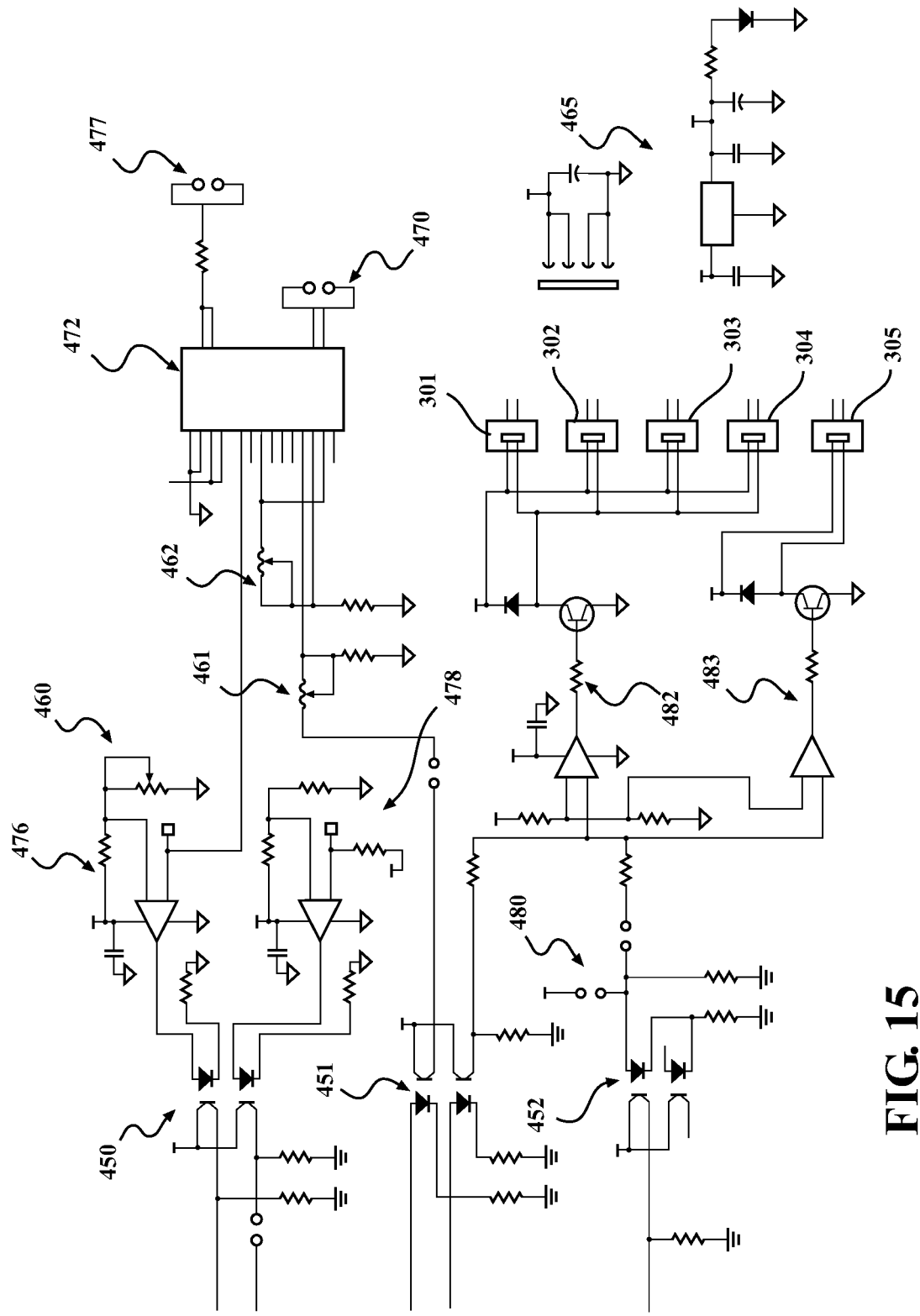
FIGS. 15 and 16 illustrate the control circuit for a controller to control at least one scanning cannula having two sweeping contacts and an LED and/or audio component for communications with the user.
Figure 16:
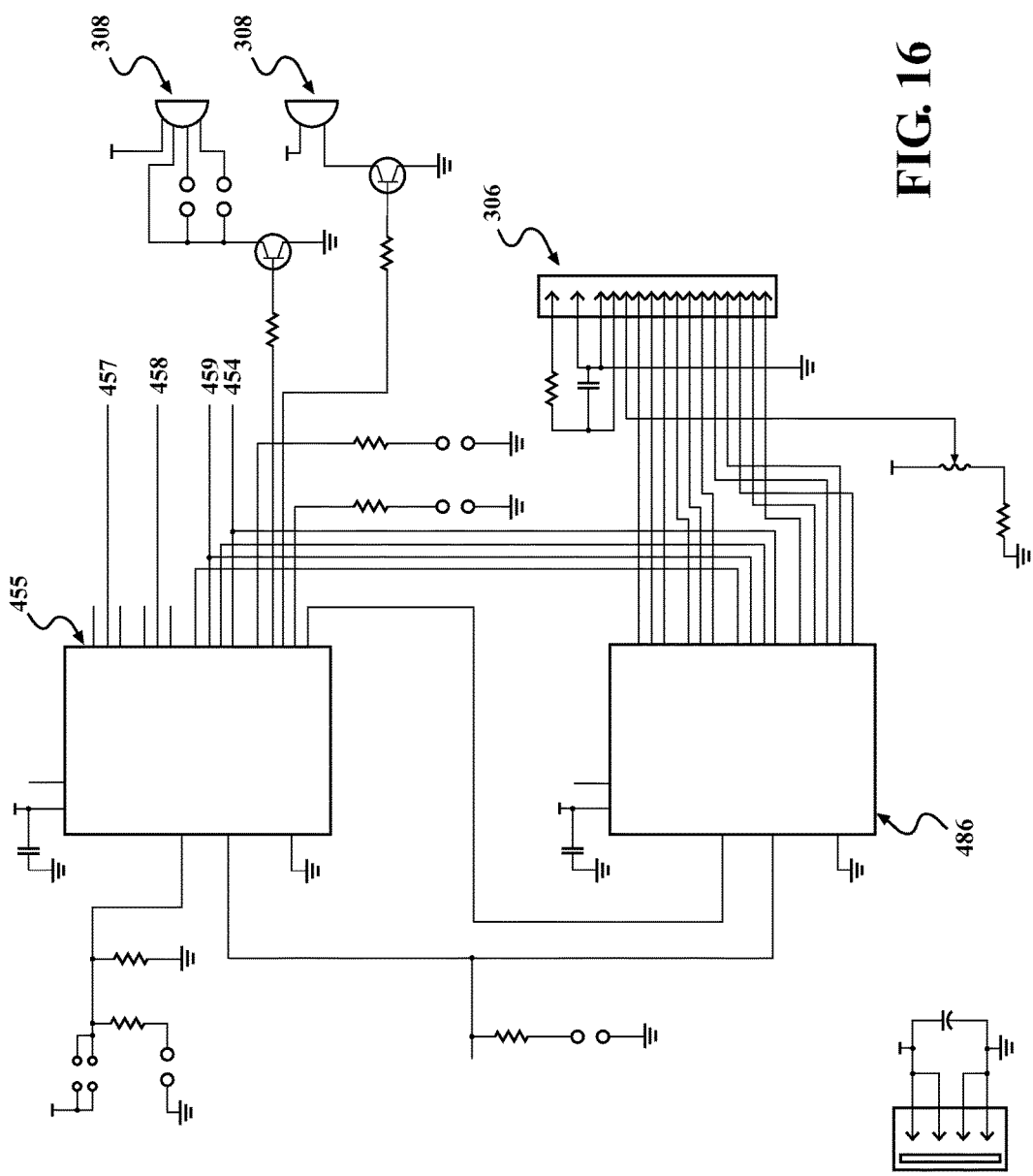
Figure 17:
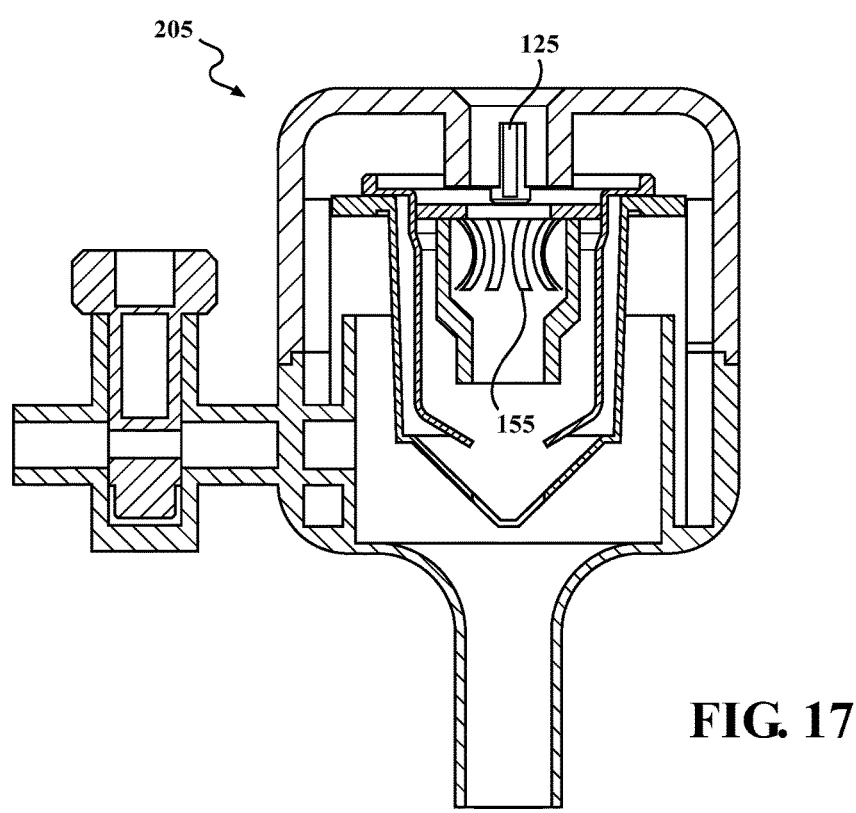
FIG. 17 shows a cross-section of an alternative embodiment of a scanning cannula with a single sweeping contact.

FIG. 14 depicts a flow chart of the functionality of software that can be used with the scanning cannula. FIGS. 15 and 16 illustrate a circuit diagram for a circuit that could be used with the software.

The circuit diagram of FIG. 16 illustrates the low voltage section, which also interacts with the high voltage section shown in FIG. 15, where a portion of the low voltage section is also shown. The low voltage section of FIG. 16 generally contains digital circuits and software which handle the control and user interfaces. The high voltage section of the FIG. 15 generally has parts which interact with the testing and the generator 140, and where the sweeping contacts (upper and lower 119, 120 or single contact 155) connect to the controller 103, and where the relays 301, 302, 303, 304 and 305 are housed. The two sections are separated to protect the more delicate circuits on the low voltage side from the high voltages present in the scanning and operation of the scanning cannula. The only link between the high voltage and low voltage sections are the optoisolators 450, 451 and 452.

Figure 21:
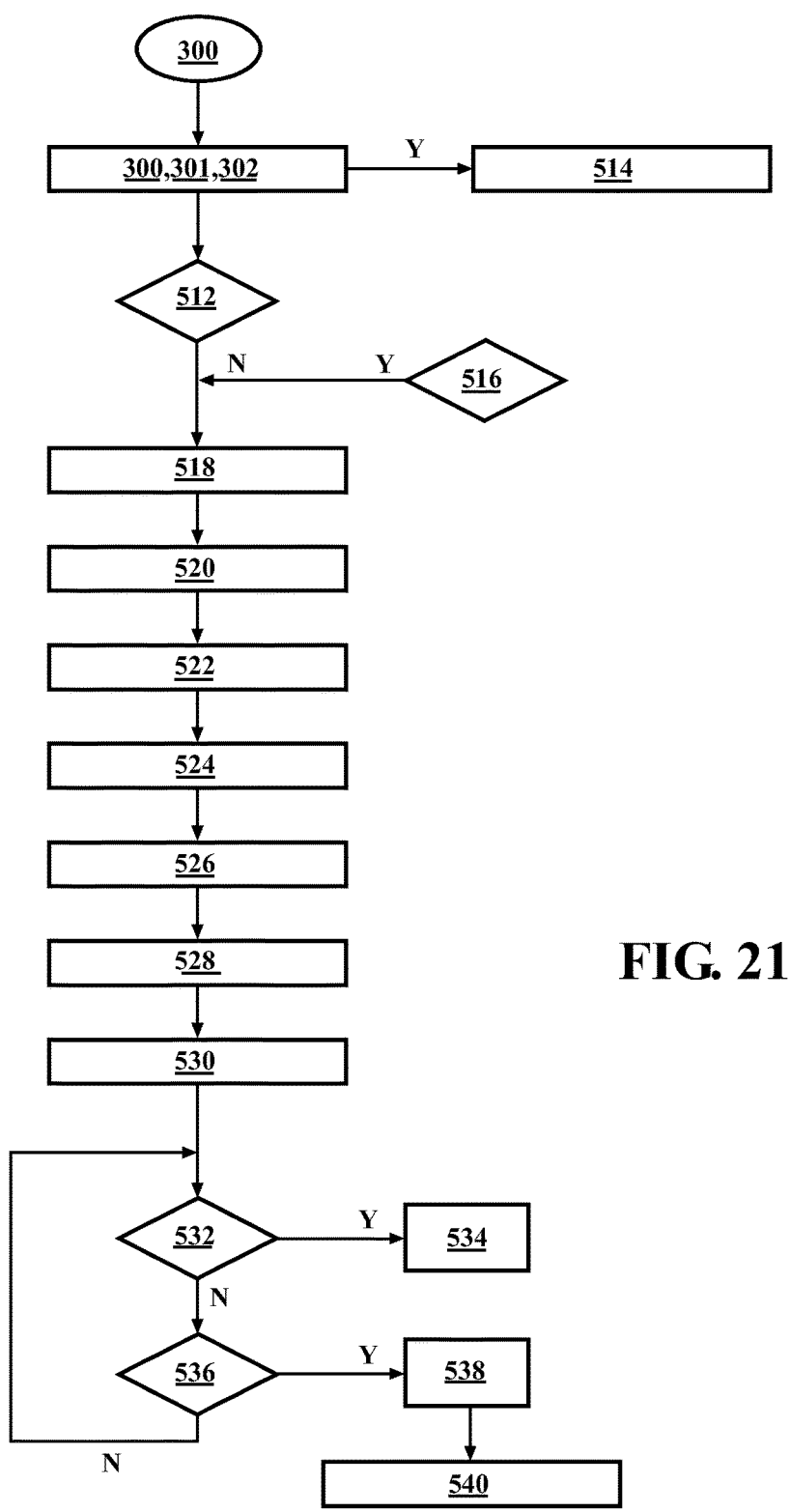
FIG. 21 depicts a flow chart of the functionality of software that can be used with the scanning cannula 205 having one sweeping contact 155.

The low voltage section of FIG. 16 has two computer chips 455 and 456. Chip 455 is the main chip and has the software described in the flowcharts set forth below, as depicted in FIG. 14 or FIG. 21. The chip 455 with its software opens and closes the relays 301, 302, 303, 304, and 305 and turns the testing high voltage supply on and off. The chip 455 with its software reads the status of the limit switch 125 and sweeping contact 155 or contacts 119, 120. It also controls the LEDs and audio signals 308, and transmits information to the second chip 456 to run the LCD display 306. The second chip 456 takes information from chip 455 and displays it on the LCD display 306. All of the connections for LEDs and audio signals, however, are driven by the main chip 455. The inputs for USC 119 or 155 is connected via port 457. Port 458 is used to connect the LSC 120 input if used. The ON/OFF power for the testing high voltage supply is connected at port 459. The relays are controlled at port 454.

All components in the high voltage section (FIG. 15) are controlled by and report to the main chip 455 through the optoisolators 450, 451, and 452. The testing high voltage supply is located in the high voltage section as are the relays and circuit to drive the lower sweeping contact. Variable resistors 460, 461, and 462 allow the adjustment of the detection threshold, the testing voltage, and the testing current, respectively. The power plug 108 of the instrument 107 connects the generator 140 via relay 301. The power plug 108 also connects to the ground of the testing circuit 470 via relay 305. The relays 302, 303, and 304 allow the connection of other lines for the instrument 107 (or other instruments) and/or the connection of a ground pad 2 to the controller 103. A connection 477 connects the power supply to the USC 119 or sweeping contact 155. Any detected arcing is amplified at circuit 476 and is transmitted to the main chip 455 via optoisolator 450.

If a lower sweeping contact 120 is used, processing is performed via circuit 478. The OVERRIDE function connects at circuit 480 to communicate with the lower voltage section via optoisolator 452.

Circuits 482 and 483 ensure that whenever relays 301, 302, 303, and 304 are open, relay 305 is closed, and vice-versa.

The software of FIG. 14 has three inputs plus a master power on/off switch and an override all disposed in the controller 103. The three inputs are from the three scanning elements, i.e., the two contacts and the limit switch.

The three scanning elements (inputs to the software) have the following functions:
1. The upper contact (high voltage) is used to scan the shaft for insulation defects.
2. The lower contact (low voltage) is used to determine whether the insulated shaft or the exposed tip of the instrument is currently being scanned by the upper contact.
3. The limit switch (also called micro-switch in our documentation) is used to determine whether or not an instrument is present in the cannula.

The software controls the following (has the following outputs):
1. The testing high voltage power supply 472 (ON/OFF). When this is ON, the upper contact is at 4000V (or whatever high voltage is selected).
2. The relays 301, 302, 303 and 304 (closed or open) that connect/disconnect the instrument 105 and ground pad 2 from the generator 140 and disconnect/connect the testing circuit ground from the power plug 108. If a test has been successfully passed or if the OVERRIDE is enabled, the relays 301, 302, 303 and 304 are closed, electrical energy flows from the generator 140 to the ground pad 2 and instrument 105 as with typical electrosurgery. At this time the relay 305 between the ground of the test circuit and the instrument 105 is open (disconnected) to protect the testing circuit from the generator 140.
3. At all other times, the relays 301, 302, 303 and 304 are open, so that the ground pad 2 and instrument 105 are disconnected from the generator 140, leaving the patient safely electrically isolated, and the relay 305 between the ground of the test circuit and the instrument is closed, allowing testing to occur.

This software also sends information to a secondary microprocessor 304 that handles the LCD display 306. The audio tones 308 and LEDs are also controlled by the software.

If the OVERRIDE actuator 404 (FIG. 20) is pressed at any time, the relays 301, 302, 303, and 304 close to allow electrosurgery, the relay 305 opens to protect the testing circuit, and the software is bypassed and does not affect the system whatsoever. The OVERRIDE actuator 404 (FIG. 20) can also be located in a position near the power switch or other locations that might serve the same purpose.

The software within the controller 103 functions after initially powering on the scanning cannula, where the relays 301, 302, 303, and 304 are open (disconnected), the relay 305 is closed, and where the testing high voltage power supply is off. Immediately upon being powered on, the controller checks the status at step 312 of the limit switch 125 to determine whether an instrument is present in the scanning cannula. If an instrument is present in the cannula upon power up, the controller displays a message at step 314 asking the user to remove it so that it may go through the scanning sequence in correct order. If the cannula is empty, the controller at step 316 requests that an instrument be inserted so that scanning may begin (the limit switch has not been activated).

Whenever the cannula is empty and powered on, the testing sequence is ready to begin. The HV supply 110 is activated at step 318 thereby bringing the upper contact 119 to 4000V. The controller 103 waits for the presence of an instrument to initiate the scanning sequence. The software returns to this state any time that the cannula is empty. From here, the system is waiting for an instrument to enter the cannula so that testing may begin.

At this point, in step 320, the relays 301, 302, 303 and 304 are still open (disconnected) and the testing high voltage supply 140 is powered on. The user is requested to insert an instrument by the LCD display 306 and the scanning cannula software waits until an instrument is present in the cannula 105 at step 322.

Once a device has entered the cannula 105, i.e., the limit switch 125 is pressed, the controller 103 waits for the upper contact 119 and then the lower contact 120 to sequentially detect the exposed tip 144 of the instrument 113, whether through arcing or direct conduction between the exposed tip 144 and the contact 119 or 120 in question. The sequential detection of the tip 144 by the two contacts 119 and 120 acts as a verification that the contacts are working properly. Thus, the software waits until the upper contact 119 detects the tip 144 of the instrument 113 at step 324 and then sequentially waits until the lower contact 120 detects the tip 144 of the instrument 113 at step 326. In general, the upper contact 119 (high-voltage) is used to scan the shaft 127 for insulation defects. The lower contact 120 (low-voltage) is used to determine whether the insulated shaft 127 or the exposed tip 144 of the instrument 107 is currently being scanned by the upper contact 119. Once the tip 144 is no longer detected by the lower (low-voltage) contact 120, the software at step 328 knows that the insulated shaft 127 of the instrument 113 is adjacent to the upper contact 119 and that the upper contact 119 is far enough away from the exposed tip 144 region so that arcing between the upper contact 119 and the tip 144 will not occur. Any arcing at the upper contact 119 from this point onward will be interpreted as an insulation defect. So, the software waits until the lower contact 120 does not detect the tip 144, and therefore it detects the insulated shaft 127.

The test of the insulated shaft 127 begins at step 330. A software based timer internal to the microprocessor software is commenced to allow a nominal amount of time (several seconds) for the surgeon to push the entire useful length of the shaft of the instrument into the cannula. Any arcing at the upper contact will be interpreted as an insulation defect. If the timer expires without an insulation defect being detected, the instrument will be deemed defect-free at step 332 and surgery will be permitted. A record of the result of the scanning test, along with the date and time of the test may be stored in the controller (or other storage media) for future reference.

If a defect is found, the user is alerted at step 334. The instrument must be removed to attempt another test.

The timer is evaluated at step 336 to determine if any time remains. If so, the software returns step 330 and repeats the process. If the allotted time has expired, and if the instrument has passed the test and is considered defect-free, the surgery is allowed by reconnecting the generator 140 to the instrument 107 and ground pad 2 at step 338. The relays close at step 340 while the testing high voltage supply is ON.

As described above, if the OVERRIDE actuator 404 is pressed at any time, the relays close to allow electrosurgery and the CB's software is bypassed and does not affect the system whatsoever. The instrument is connected to the generator (generator relay is closed). To protect the testing circuit from the generator waveform, the relay 305 from the instrument power plug 480 to the controller 105 ground is open.

For this reason, the functionality of the OVERRIDE actuator 404 (FIG. 20) may be included in the flowchart at any point in the flowchart. The OVERRIDE actuator 404 (FIG. 20) can be located at the power switch or other locations, e.g., the top of the scanning cannula 105, which might serve the same purpose.

FIGS. 13, 13A, 13B, 13C, 18A, 18B, and 18C show an alternative design of the Attachable Scanning Portion (ASP) 205 or 233 that may be attached to commercially available conventional cannulas 123. This added variant expands the usability of the scanning benefits to virtually all existing cannulas, providing said available cannulas are made of non-conductive materials, such as non-conductive plastics, etc. The ASP 205 or 233 will be attached to the cannula 123 by the same mechanical mechanism as the trocar 145 was attached prior to removal, or it can alternatively have its own separate attachment mechanism. Only one sweeping contact 155 is being used in the example shown in FIGS. 18A, 18B, and 18C. Double sweeping contacts are shown in FIGS. 13, 13A, 13B, and 13C.

With reference to FIGS. 13, 13A, 13B and 13C, the cannula 123 has slots 234 into which tabs 238 from the ASP 233 conformably attach and detach. The tabs 238 are controlled via a strap (see FIG. 18D) having buttons 239. As the buttons are manually pushed into the ASP 233 (or 205 in FIG. 18A), the tabs 238 are forced toward the center axis of the ASP 233 (or 205) to release the contact with the slots 234, and release the ASP 233 (or 205) from the cannula 123. The process is reversed when the ASP 233 (or 205) is attached to the cannula 123.

Figure 18C:
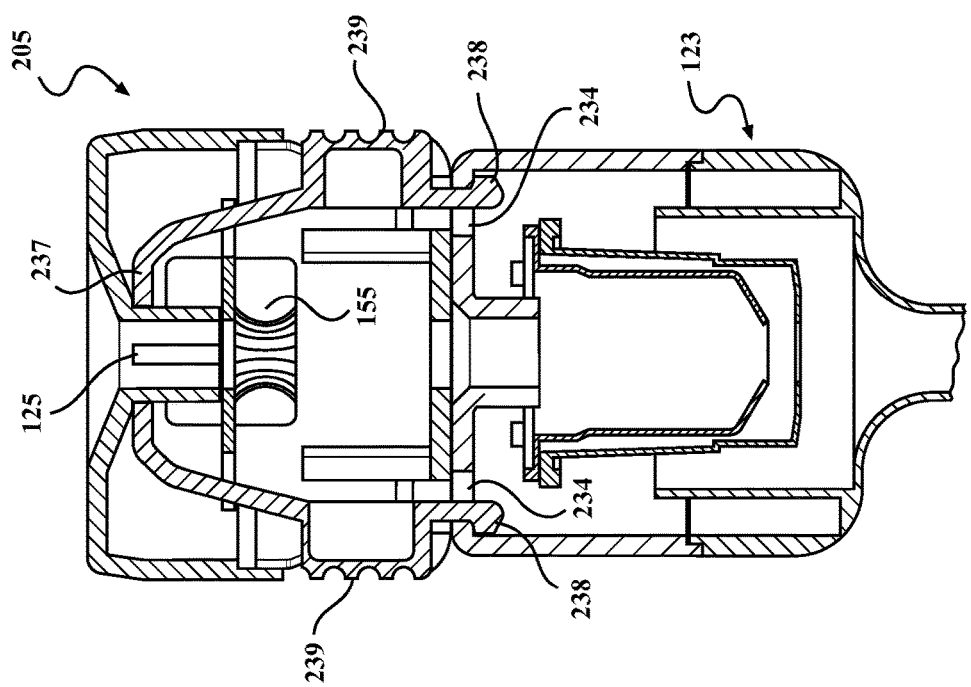
Figure 18B:
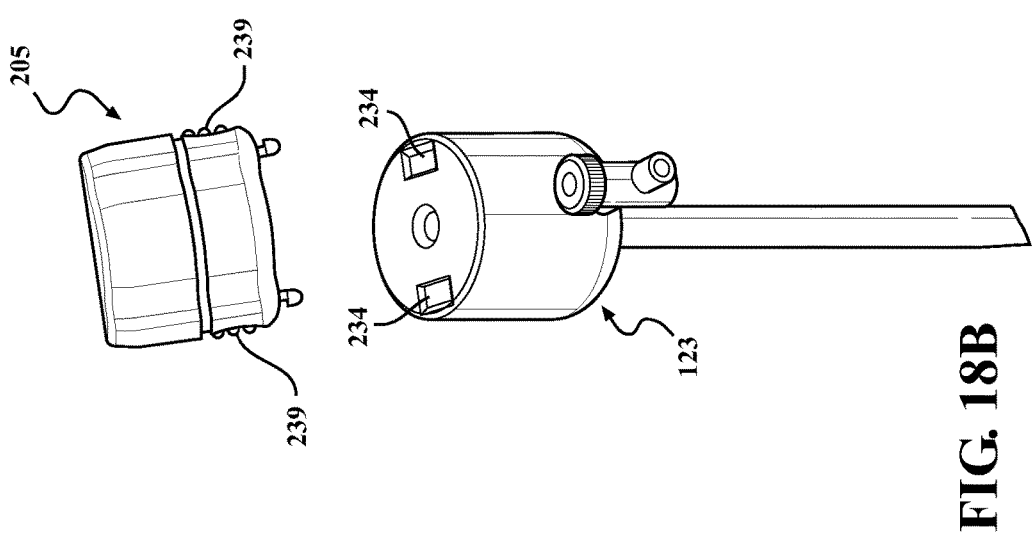

In the variant shown in FIGS. 18A, 18B, and 18C, once micro-switch 125 is tripped, the sweeping contact 155 is charged initially with low voltage that is enough to "sense" the incoming conducting distal tip end of a monopolar device. Once the current flow through the instrument ceases, the voltage is raised instantaneously to high voltage for the remainder of the scanning. In another alternative for the single sweeping contact version of FIGS. 18A, 18B, and 18C, the sweeping contact is at approximately 3000V-4000V initially unless a test has been passed or failed. This means that the device will not wait for the micro-switch 125. This may allow faster and more reliable results because there would be no start-up transition time when first activating a testing high voltage supply.

FIG. 21 depicts a flow chart of the functionality of software that can be used with the scanning cannula 205 having one sweeping contact 155. The controller 103 can use the same circuit (FIGS. 15 and 16) used with the new software as described here.

The software has two inputs plus a master power on/off switch and an override all disposed in the controller 103. The override switch may also be disposed on the cannula 205. The two inputs are from the two scanning elements, i.e., the one sweeping contact 155 and the limit switch 125.

The two scanning elements (inputs to the software) have the following functions:
 1. The single sweeping contact 155 (high voltage) is used to scan the shaft 127 for insulation defects and to determine which part of the instrument 107 (exposed tip (jaws 144) or insulated shaft 127) is currently being scanned.
 2. The limit switch 125 (also called micro-switch) is used to determine whether or not an instrument 107 (or a trocar 145) is present in the cannula 205.

The software controls the following (has the following outputs):
 1. The high voltage power supply (ON/OFF) 459. When this is ON, the upper contact is at approximately 4000V (or whatever high voltage is selected, such as approximately 3000V).
 2. Relays 301, 302, 303 and 304 (closed or open) that connect/disconnect the instrument 107 and ground pad 2 from the generator 140 and a relay 305 that disconnects/connects the controller ground 470 from the instrument power plug 108. When the relays 301, 302, 303, and 304 are closed, electrical energy flows from the generator 140 to the ground pad 2 and instrument power plug 108 as with typical electrosurgery. When the relays 301, 302, 303 and 304 are open, the ground pad 2 and instrument 107 are disconnected from the generator 140, leaving the patient safely electrically isolated. When the controller 103 ground to instrument power plug relay 305 is open the controller 103 circuits are safely isolated from the generator 140. When this relay 305 is closed, the instrument power plug 108 is connected to the controller 103 ground to allow a scanning test to proceed.

This software also sends information to a secondary microprocessor 304 that handles the LCD display 306. The LED display 306 and/or audio tones 308 are also controlled by the software.

If the OVERRIDE actuator 404 is pressed at any time, the relays 301, 302, 303 and 304 close to allow electrosurgery and cancel the scanning as applicable, and the software is bypassed to not affect the system whatsoever. For this reason, the OVERRIDE actuator 404 can also be located in a position near the power switch or other locations that might serve the same purpose.

The software within the controller 103 functions after initially powering on the scanning cannula 205, where the relays 301, 302, 303 and 304 are open (disconnected) and where the high voltage power supply via the generator 140 is off. Immediately upon being powered on, the controller 103 checks the status at step 512 of the limit switch 125 to determine whether an instrument is present in the cannula 205. If an instrument is present in the cannula 205 upon power up, the controller displays a message at step 514 asking the user to remove it so that it may go through the scanning sequence in correct order. If the cannula 205 is empty, the controller 103 at step 516 requests that an instrument be inserted so that scanning may begin (the limit switch 125 has not been activated).

Now the testing sequence is ready to begin. The HV supply 472 is activated at step 518 thereby bringing the contact 155 to approximately 4000V. The controller 103 waits for the presence of an instrument (such as 107) to initiate the scanning sequence. The software returns to this state any time that the cannula 205 is empty. From here, the system is waiting for an instrument to enter the cannula 205 so that testing may begin.

At this point, in step 520, the relays 301, 302, 303 and 304 are still open (disconnected), and the testing high voltage supply 472 is powered on. The relay 305 is closed so that testing may proceed. The user is requested to insert an instrument by the LCD display 306 and the scanning cannula software waits until an instrument is present in the cannula 205 at step 522.

Once a device has entered the cannula 205, i.e., the limit switch 125 is contacted, the controller 103 waits for the single contact 155 to detect the exposed tip 144 of the instrument 113 at step 524, whether through arcing or direct conduction between the exposed tip 144 and the contact 155 in question. Once the tip 144 is no longer detected by the contact 155 at step 526, the software at step 528 has the program wait a predetermined amount of time (usually a couple of milliseconds, for example) to know that the insulated shaft 127 of the instrument 107 is adjacent to the contact 155 and that the contact 155 is far enough away from the exposed tip 144 region so that arcing between the contact 155 and the tip (jaws 144) will not occur. Any arcing at the contact 155 from this point onward will be interpreted as an insulation defect. So, the software waits the predetermined time to permit the user to push the shaft further into the cannula after the contact 155 does not detect the tip (jaws 144), and therefore it detects the insulated shaft 127.

The test of the insulated shaft 127 begins at step 530. A software based timer is commenced to allow a nominal amount of time (several seconds) for the surgeon to push the entire useful length of the shaft of the instrument into the cannula 205. Any arcing at the upper contact will be interpreted as an insulation defect. If the timer expires without an insulation defect being detected, the instrument will be deemed defect-free at step 532 and surgery will be permitted. This test applies here to either an attachable scanning device or an integrated cannula/scanning device, and the attachable scanning device can be attached with either one sweeping contact or two.

If a defect is found, the user is alerted at step 534. The instrument must be removed to attempt another test. A record of the result of the scanning test, along with the date and time of the test, may be stored in the controller (or other storage medium) for future reference.

The test timer is evaluated at step 536 to determine if testing time remains. If so, the system continues to wait for an insulation defect to be detected or for the testing time to expire. If time has elapsed and no defects have been found, the instrument has passed the test and is considered defect free. Electrosurgery is allowed by reconnecting the generator 140 and ground pad 2 at step 538. The relays 301, 302, 303 and 304 close at step 540 while the high voltage supply is off. The relay 305 is opened to protect the testing circuits.

As described above, if the OVERRIDE actuator 404 is pressed at any time, the relays close to allow electrosurgery and the software is bypassed and does not affect the system whatsoever. The instrument 107 is connected to the generator 140 (generator relay 301 is closed). To protect the testing circuit from the generator waveform, the testing circuit ground relay 305 is open.

For this reason, the functionality of the OVERRIDE actuator 404 may be included in the flowchart at any point in the flowchart, and the OVERRIDE actuator 404 can also be located at the power switch or other locations, e.g., the top of the attachable scanning cannula head 205 or 233, that might serve the same purpose.

The same circuit can be used for the single contact as is used for the two sweeping contacts, as described above and FIGS. 15 and 16, but with different software as shown in FIG. 21.

FIG. 19 shows a typical situation where multiple scanning cannulas 105 are used in the same operation on a patient 1. Each scanning cannula or attachable head 105 or 205 (or 233) is connected to a connector manifold 226 via scanning cannula cable 6 or 106. Connecting manifold 226 is connected to the controller 103 via multi-channel cable 227. This typical connection of multiple scanning cannulas 105 allows the usage of a single power source (the ESU/generator) 140 with various instruments as the instrument to be used has to be connected to cable 9 prior to insertion into a selected scanning cannula 105. Following the short scan, once found to be free of defects, an activation of the ESU 140 via a foot switch (not shown) or the instrument's integrated activation buttons (FIG. 20) will direct the RF energy to the connected instrument 107.

Figure 20:
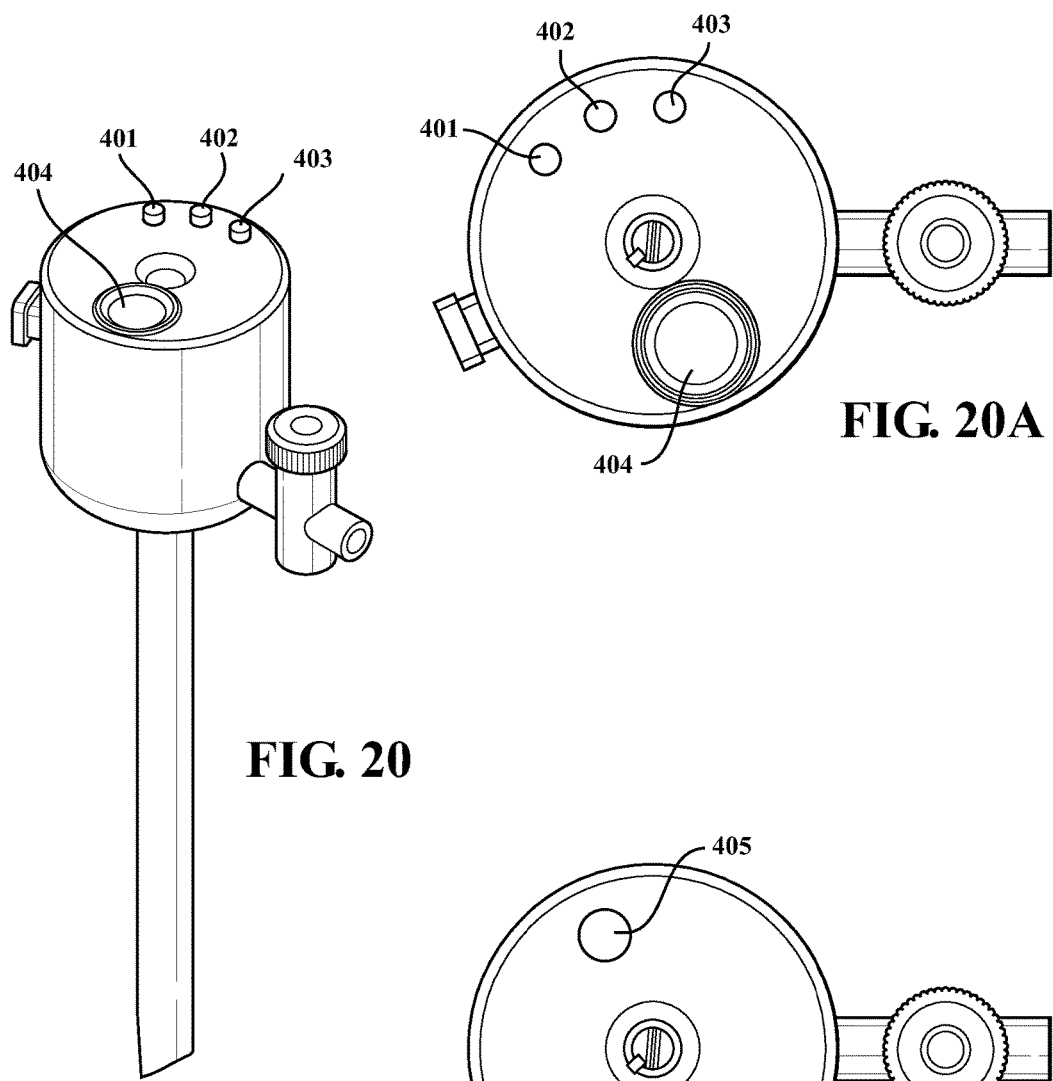

FIG. 20 depicts the interface between the user and the scanning cannula controller. The scanning cannula (SC) may be equipped with one or more LEDs as shown in FIGS. 20 and 20A. An OVERRIDE actuator 404 is shown to activate the OVERRIDE function described above for the scanning cannula 105 or 205.

As an example, while using 3 LEDs:
LED 401 is blue
LED 402 is green
LED 403 is red An example algorithm for the LEDs 401, 402, 403 is as follows:
1. LED 401 (blue) is on steady once the scanning cannula is attached to the controller 103. It flashes once the override button 404 is depressed, and goes back to steady blue only when the instrument that was inserted subject to the override command has been removed.
2. LED 402 (green) is turned on and flashing during the scan. LED 402 is on steady green after a positive scan as long as the passed instrument stays inside the scanning cannula. LED 402 is off when the instrument was removed or its scan failed.
3. LED 403 (red) is turned on flashing when a scan ends with negative results. It stays on flashing until the instrument is removed outside the scanning cannula or the OVERRIDE button is pressed.

The same algorithm may be used for another design variant, where instead of using three LEDs, a single tri-color LED 405 is used. Audio tones may also be substituted for the lights of the LEDs or used concurrently with the LED lights.

Any combination of the above described embodiments is within the scope of the invention.

Although the present invention has been described in relation to endoscopic applications, the principles and the basic design of the scanning chamber 24 may apply to many industrial and general fields, where simple scanning of dielectric barrier defects is required. Further, even though a wireless embodiment is described herein, the same scanning principles may apply to a wired scanning cannula, i.e., a similar device that is wired to a controller with a multi-channel cable, branched and connected to the scanning cannula 10 at scanning chamber 24.

Although the invention has been described by reference to specific embodiments, it should be understood that numerous changes may be made within the spirit and scope of the inventive concepts described. Accordingly, it is intended that the invention not be limited to the described embodiments unless the claims are specifically worded to do so, but otherwise that it have the full scope defined by the language of the following claims.

The invention claimed is:
1. A scanning cannula comprising:
an elongated tubular element configured to be inserted into a body having a receiving end, an opposite exit end, and a passageway extending from said receiving end to said opposite exit end configured to receive an electrosurgical instrument;
a housing integral with the elongated tubular element at said receiving end;
at least one sweeping contact disposed solely in said housing at the receiving end of said elongated tubular element;
at least one controller; and
wherein an electrosurgical instrument is configured to be inserted into said receiving end of said elongated tubular element and pass through said at least one sweeping contact while a portion of said scanning cannula is disposed in the body, and any electrical insulation defect of the electrosurgical instrument detected by said at least one sweeping contact is relayed as an error signal to said at least one controller.
2. The scanning cannula of claim 1, wherein said at least one sweeping contact is a disk-shaped ring including a plurality of fingers extending from a hollow center of a ring.
3. The scanning cannula of claim 1, further comprises a communication device including a cable that electrically transmits signals to the controller.
4. The scanning cannula of claim 1, including a limit switch disposed in said passageway upstream of said at least one sweeping contact, said limit switch being electrically connected to said at least one controller, wherein said limit switch detects the presence of said electrosurgical instrument in said passageway.
5. The scanning cannula of claim 1, further comprises a circuit including a capacitor electrically connected to said at least one sweeping contact.
6. The scanning cannula of claim 5, wherein said circuit includes two or more LEDs that display status information.
7. A scanning cannula assembly comprising:
a cannula configured to be inserted into a body via an aperture in the body, having a receiving end, an opposite exit end, and a passageway extending from said receiving end to said opposite exit end and configured to receive an electrosurgical instrument while said scanning cannula is disposed at least in part within the body;
a housing connected to said scanning cannula at said receiving end;
at least one sweeping contact disposed integrally and solely within the housing,
at least one circuit;
at least one receiver to receive signals from said at least one circuit; and
wherein said electrosurgical instrument is configured to be inserted into said receiving end of said scanning cannula and pass through at least one sweeping contact while a portion of said cannula is disposed in the body, and any electrical insulation defect of the electrosurgical instrument detected by said at least one sweeping contact is relayed as an error signal to said at least one circuit to communicate said error signal to said at least one receiver.
8. A scanning cannula device for scanning an electrosurgical instrument for electrical insulation defects comprising:
an elongated cannula configured to be inserted into a body having a receiving end with a head portion, an opposite exit end, and a passageway extending from said receiving end to said opposite exit end;
at least one sweeping contact disposed solely in said head portion;
a circuit disposed in the head portion of said scanning cannula, said at least one sweeping contact being electrically connected to said circuit;
a communication device connected to said circuit to transmit signals from said circuit to a controller of said electrosurgical instrument; and
wherein said electrosurgical instrument is configured to be inserted into said receiving end of said scanning cannula and pass through said at least one sweeping contact, and any electrical insulation defect of the electrosurgical instrument detected by said at least one sweeping contact is relayed as an error signal to said circuit, which communicates the error signal to the controller.
9. The scanning cannula device of claim 8, wherein the head portion is detachable from the remaining portion of the scanning cannula.
10. An electrosurgical system for scanning an electrosurgical instrument for electrical insulation defects, said electrosurgical system comprising:
a scanning cannula including a cannula having a receiving end, an opposite exit end, and a passageway extending from said receiving end to said opposite exit end;
a housing at said receiving end;
at least one sweeping contact disposed solely in said housing;

a circuit associated with said housing, said at least one sweeping contact being electrically connected to said circuit;

a communication device connected to said circuit to transmit signals from said circuit;

a controller in communication with said circuit;

an electrosurgical generator electrically connected to said controller;

an electrosurgical instrument electrically connected to said controller; and wherein said electrosurgical instrument is configured to be inserted into said receiving end of said cannula and pass through said at least one sweeping contact, and any electrical defect of said electrosurgical instrument detected by said at least one sweeping contact is relayed as an error signal to said circuit, which communicates the error signal to said controller.

11. An electrosurgical system for scanning an electrosurgical instrument for electrical insulation defects, said system comprising:

a scanning cannula including:

an elongated portion configured to be placed into a body of a patient, having a receiving end, an opposite exit end, and a passageway extending from said receiving end to said opposite exit end;

a housing disposed at said receiving end; and at least one sweeping contact disposed solely in said housing and spaced from said exit end of said cannula; and a circuit electrically connected to said at least one sweeping contact;

a communication device connected to said circuit to transmit signals from said circuit;

a controller in communication with said scanning cannula;

an electrosurgical generator electrically connected to said controller; and an electrosurgical instrument electrically connected to said controller;

wherein said electrosurgical instrument is inserted into said receiving end of said scanning cannula and passes through said at least one sweeping contact, and any electrical insulation defect of said electrosurgical instrument detected by said at least one sweeping contact is relayed as an error signal to said circuit, which communicates the error signal to said controller.

12. The electrosurgical system of claim 11, wherein said communication device includes a cable that is electrically connected to said circuit and said controller, and said circuit communicates with said controller through said cable.

13. The electrosurgical system of claim 11, wherein upon receiving the error signal from said scanning cannula, an override can be implemented by the user in order to bypass the circuit and a testing of said electrosurgical instrument.

14. A scanning cannula assembly comprising:

a cannula configured to be inserted into a body via an aperture in the body, having a receiving end, an opposite exit end, and a passageway extending from said receiving end to said opposite exit end configured to receive an electrosurgical instrument while said scanning cannula is disposed at least in part within the body;

a head portion at the receiving end of said cannula;

at least one sweeping contact disposed solely within said head portion of said cannula;

at least one circuit; and at least one receiver configured to receive signals from said circuit;

wherein an electrosurgical instrument is configured to be inserted into said receiving end of said cannula and pass through at least one sweeping contact while a portion of said cannula is disposed in the body, and any electrical insulation defect of the electrosurgical instrument detected by said at least one sweeping contact is relayed as an error signal to said at least one circuit to communicate an error signal to the at least one receiver;

wherein the head portion is detachable from the remaining portion of the cannula; and wherein said sweeping contact is a disk-shaped ring including a plurality of fingers extending axially from a hollow center of said ring.

15. The scanning cannula assembly of claim 14, wherein the head portion is configured to be re-attachable to said cannula or attachable to another cannula.

16. A scanning cannula assembly comprising:

a cannula configured to be inserted into a body via an aperture in the body, having a receiving end, an opposite exit end, and a passageway extending from said receiving end to said exit end configured to receive an electrosurgical instrument while said cannula is disposed at least in part within the body;

a detachable head portion;

at least one sweeping contact disposed integrally within said detachable head portion of the cannula and detachable with said head portion;

at least one circuit;

at least one receiver to receive signals from said at least one circuit;

wherein an electrosurgical instrument is configured to be inserted into said receiving end of said cannula and pass through at least one sweeping contact while a portion of said cannula is disposed in the body, and any electrical insulation defect of the electrosurgical instrument detected by said at least one sweeping contact is relayed as an error signal to said at least one circuit to communicate said error signal to said at least one receiver, and wherein the head portion is detachable from the remaining portion of the cannula; and wherein said at least one sweeping contact is a disk-shaped ring including a plurality of fingers extending axially from a hollow center of said ring.

17. The scanning cannula assembly of claim 16, including a limit switch disposed in said passageway upstream of said at least one sweeping contact, said limit switch being electrically connected to said at least one circuit, wherein said limit switch detects the presence of said electrosurgical instrument in said passageway.

18. The scanning cannula assembly of claim 16, wherein said at least one circuit includes a capacitor electrically connected to each of said at least one sweeping contact.

19. The scanning cannula assembly of claim 16, wherein at least one sweeping contact comprises only one sweeping contact that is disposed in said passageway; said only one sweeping contact is configured to be electrically connected to said circuit; wherein said electrosurgical instrument inserted into said receiving end of said cannula passes through said only one sweeping contact, and any electrical insulation defect of the electrosurgical instrument detected by said only one sweeping contact is relayed as the error signal to said at least one circuit, which communicates the error signal to the controller.

20. A scanning cannula assembly comprising:

a cannula configured to be inserted into a body via an aperture in the body, having a receiving end, an opposite exit end, and a passageway extending from said receiving end to said opposite exit end configured to receive an electrosurgical instrument while said cannula is disposed at least in part within the body;

a head portion is disposed at the receiving end of said cannula;

at least one sweeping contact disposed solely within said head portion of said cannula;

at least one circuit;

at least one receiver to receive signals from said at least one circuit;

wherein said electrosurgical instrument is configured to be inserted into said receiving end of said cannula and pass through said at least one sweeping contact while a portion of said cannula is disposed in the body, and any electrical insulation defect of the electrosurgical instrument detected by said at least one sweeping contact is relayed as an error signal to said at least one circuit to communicate said error signal to said at least one receiver; and an override mechanism configured to override a result of said cannula during electrosurgical instrument scanning.

\* \* \* \* \*